US008317857B2

(12) United States Patent
Shokoohi et al.

(10) Patent No.: US 8,317,857 B2
(45) Date of Patent: Nov. 27, 2012

(54) BIODEGRADABLE SELF-EXPANDING PROSTHESIS

(75) Inventors: Mehrdad Mike Shokoohi, Miami, FL (US); Juan F. Granada, Upper Saddle River, NJ (US)

(73) Assignee: Telesis Research, LLC, Coral Gables, FL (US)

( * ) Notice: Subject to any disclaimer, the term of this patent is extended or adjusted under 35 U.S.C. 154(b) by 360 days.

(21) Appl. No.: 12/503,762

(22) Filed: Jul. 15, 2009

(65) Prior Publication Data
US 2010/0016940 A1  Jan. 21, 2010

Related U.S. Application Data

(63) Continuation-in-part of application No. 11/972,406, filed on Jan. 10, 2008.

(51) Int. Cl.
*A61F 2/06* (2006.01)

(52) U.S. Cl. ............ 623/1.42; 623/1.11; 623/1.34; 623/1.35; 623/1.46

(58) Field of Classification Search .......... 623/1.15, 623/1.42–1.46, 1.49–1.51, 1.53
See application file for complete search history.

(56) References Cited

U.S. PATENT DOCUMENTS

| | | | |
|---|---|---|---|
| 4,655,771 A | 4/1987 | Wallsten | |
| 4,954,126 A | 9/1990 | Wallsten | |
| 5,026,377 A | 6/1991 | Burton et al. | |
| 5,061,275 A | 10/1991 | Wallsten et al. | |
| 5,176,907 A | 1/1993 | Leong | |
| 5,194,581 A | 3/1993 | Leong | |
| 5,256,765 A | 10/1993 | Leong | |
| 5,342,348 A * | 8/1994 | Kaplan | 604/891.1 |
| 5,527,337 A | 6/1996 | Stack et al. | |
| 5,545,208 A | 8/1996 | Wolff et al. | |
| 5,551,954 A | 9/1996 | Buscemi et al. | |
| 5,630,840 A | 5/1997 | Mayer | |
| 5,645,559 A | 7/1997 | Hachtman et al. | |
| 5,667,523 A | 9/1997 | Bynon et al. | |
| 5,700,901 A | 12/1997 | Hurst et al. | |
| 5,718,159 A | 2/1998 | Thompson | |
| 5,741,333 A | 4/1998 | Frid | |
| 5,997,468 A | 12/1999 | Wolff et al. | |
| 6,042,578 A | 3/2000 | Dinh et al. | |
| 6,156,064 A * | 12/2000 | Chouinard | 623/1.44 |
| 6,245,103 B1 | 6/2001 | Stinson | |
| 6,295,714 B1 | 10/2001 | Roychowdhury et al. | |
| 6,551,352 B2 | 4/2003 | Clerc et al. | |

(Continued)

OTHER PUBLICATIONS

International Search Report dated Sep. 14, 2010 PCT/US2010/042013 in 12 pages.

(Continued)

*Primary Examiner* — Thomas J Sweet
*Assistant Examiner* — Yashita Sharma
(74) *Attorney, Agent, or Firm* — Knobbe, Martens, Olson & Bear LLP

(57) ABSTRACT

Disclosed herein is a biodegradable prosthesis that includes a first end, a second end, and an elongate tubular body with a lumen therethrough. The prosthesis can have a first layer comprising a set of flexible interbraided bioabsorbable filaments, and optionally a set of flexible interbraided metallic filaments. Also, the prosthesis can have a second layer comprising a porous thermoplastic material that can be either an outer layer or an inner layer relative to the first layer. The prosthesis can include other features including branch apertures, folded portions, and attachment mechanisms for the first and second layers.

18 Claims, 25 Drawing Sheets

U.S. PATENT DOCUMENTS

| | | |
|---|---|---|
| 6,626,939 B1 | 9/2003 | Burnside et al. |
| 6,652,582 B1 | 11/2003 | Stinson |
| 6,719,934 B2 | 4/2004 | Stinson |
| 6,991,647 B2 | 1/2006 | Jadhav |
| 6,997,948 B2 | 2/2006 | Stinson |
| 7,001,425 B2 | 2/2006 | McCullagh et al. |
| 7,163,555 B2 | 1/2007 | Dinh |
| 7,226,473 B2 * | 6/2007 | Brar et al. .................... 623/1.11 |
| 2001/0056299 A1 | 12/2001 | Thompson |
| 2002/0147492 A1 | 10/2002 | Shokoohi et al. |
| 2004/0162606 A1 | 8/2004 | Thompson |
| 2004/0167606 A1 | 8/2004 | Chouinard |
| 2004/0193241 A1 | 9/2004 | Stinson |
| 2005/0209676 A1 | 9/2005 | Kusleika |
| 2005/0283224 A1 * | 12/2005 | King ........................... 623/1.13 |
| 2006/0052859 A1 | 3/2006 | Igaki |
| 2006/0057183 A1 | 3/2006 | Nakano et al. |
| 2006/0058867 A1 | 3/2006 | Thistle et al. |
| 2006/0070516 A1 | 4/2006 | McCullagh et al. |
| 2006/0129222 A1 | 6/2006 | Stinson |
| 2006/0195175 A1 * | 8/2006 | Bregulla ....................... 623/1.15 |
| 2006/0224234 A1 | 10/2006 | Jayaraman |
| 2006/0266474 A1 | 11/2006 | Burnside et al. |
| 2007/0123977 A1 * | 5/2007 | Cottone et al. ............... 623/1.42 |
| 2007/0255394 A1 | 11/2007 | Ryan |
| 2008/0234799 A1 | 9/2008 | Acosta et al. |
| 2008/0255653 A1 | 10/2008 | Schkolnik |
| 2009/0182404 A1 | 7/2009 | Shokoohi et al. |

OTHER PUBLICATIONS

Leach et al., *Degradation of double-walled microspheres of PLLA and P(CPP:SA) 20:80. I. In vitro degradation*, Biomaterials 19 (1998) pp. 1973-1980.

Xu et al., *Polyphosphoester microspheres for sustaining release of biologically active nerve growth factor*, Biomaterials 23 (2002) pp. 3765-3772.

Shi et al., *Double walled POE/PLGA microspheres: encapsulation of water-soluble and water-insoluble proteins and their release properties*, Journal of Controlled Release 89 (2003) pp. 167-177.

Yang et al., *POE/PLGA composite microspheres: formation and in vitro behavior of double walled microspheres*, Journal of Controlled Release 88 (2003) pp. 201-213.

Berkland et al., *Uniform double-walled polymer microspheres of controllable shell thickness*, Journal of Controlled Release 96 (2004) pp. 101-111.

Pollauf et al., *Use of thermodynamic parameters for design of double-walled microsphere fabrication methods*, Biomaterials 27 (2006) pp. 2898-2906.

Mao, et al., "Biodegradable poly(terephthalate-co-phosphate)s: synthesis, characterization and drug-release properties", J. Biomater Sci Polym Ed. 2005; 16(2): pp. 135-161.

International Search Report for PCT/US09/30485 mailed Mar. 3, 2009.

* cited by examiner

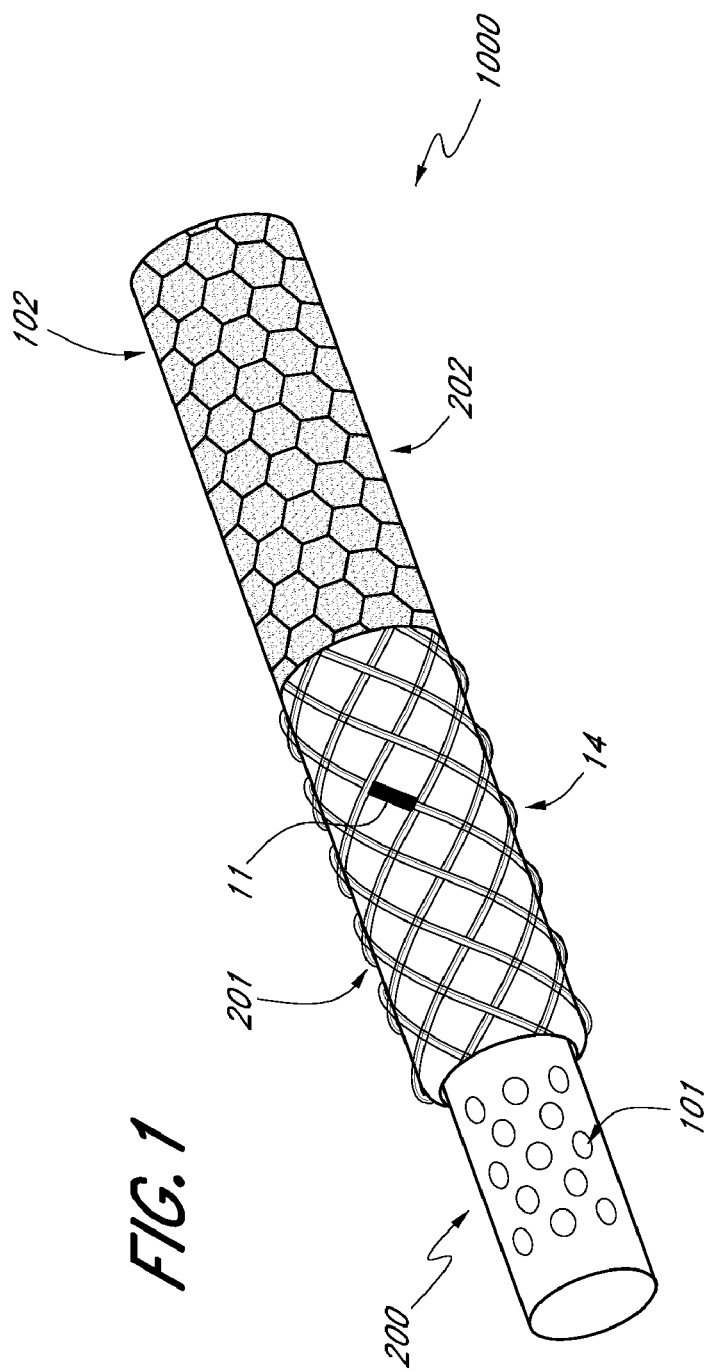

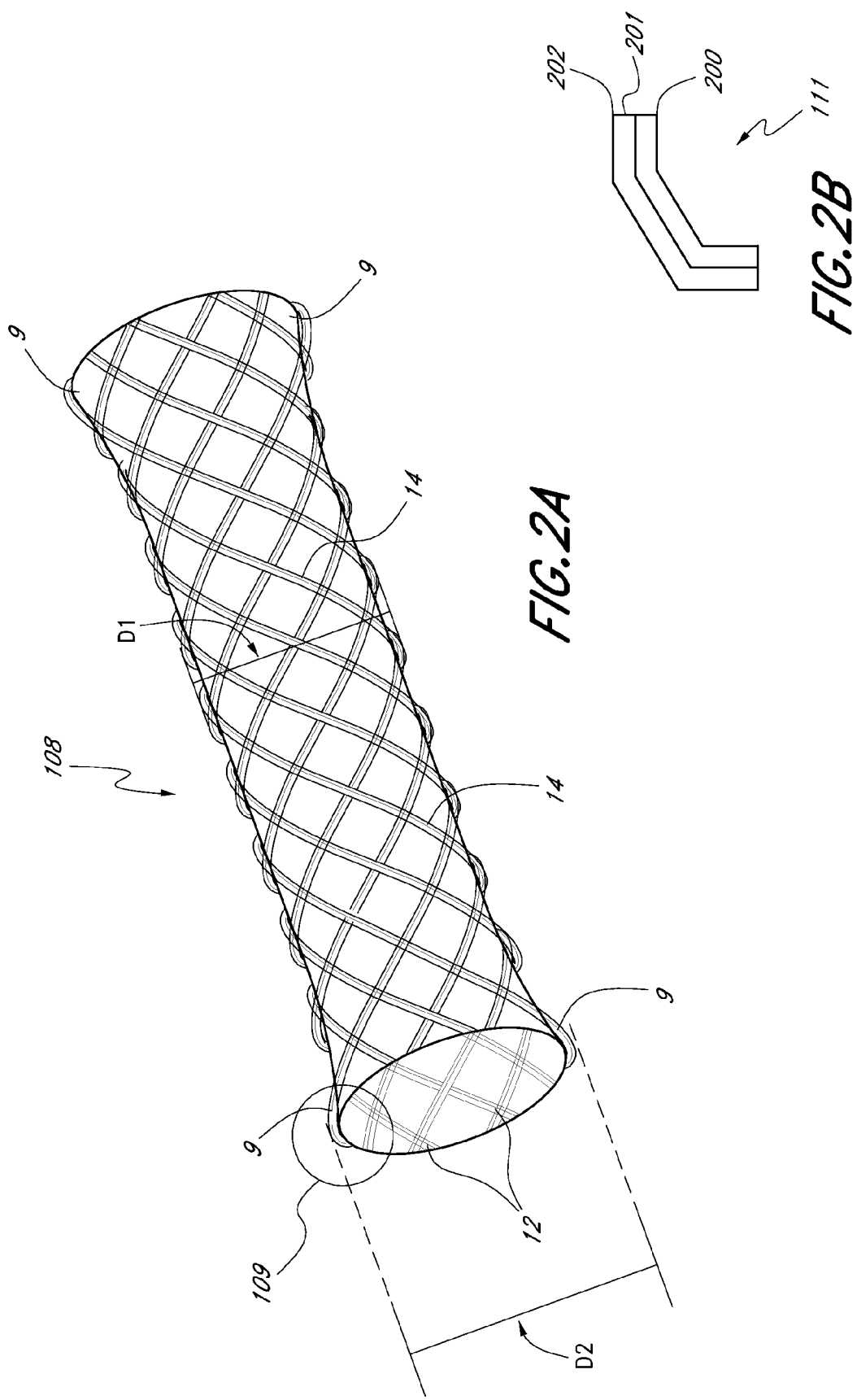

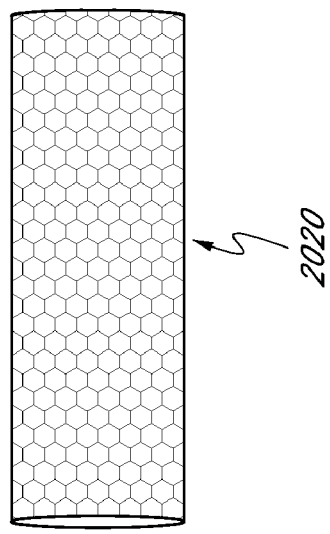
+
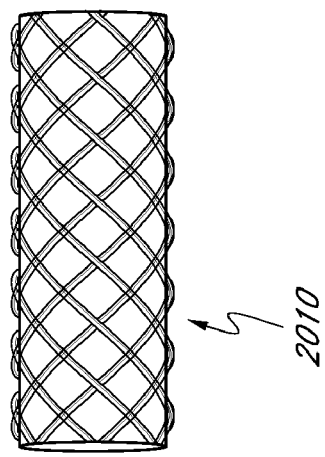
+
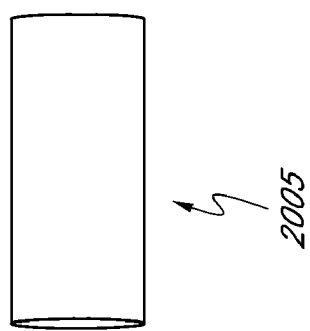
FIG.2C

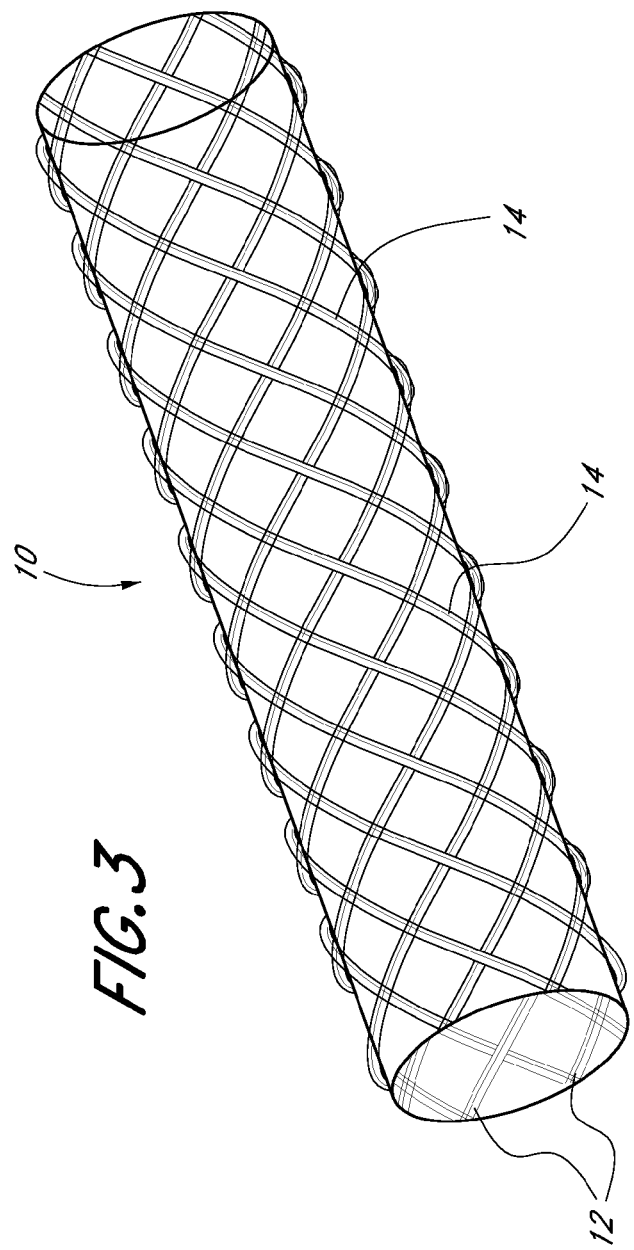

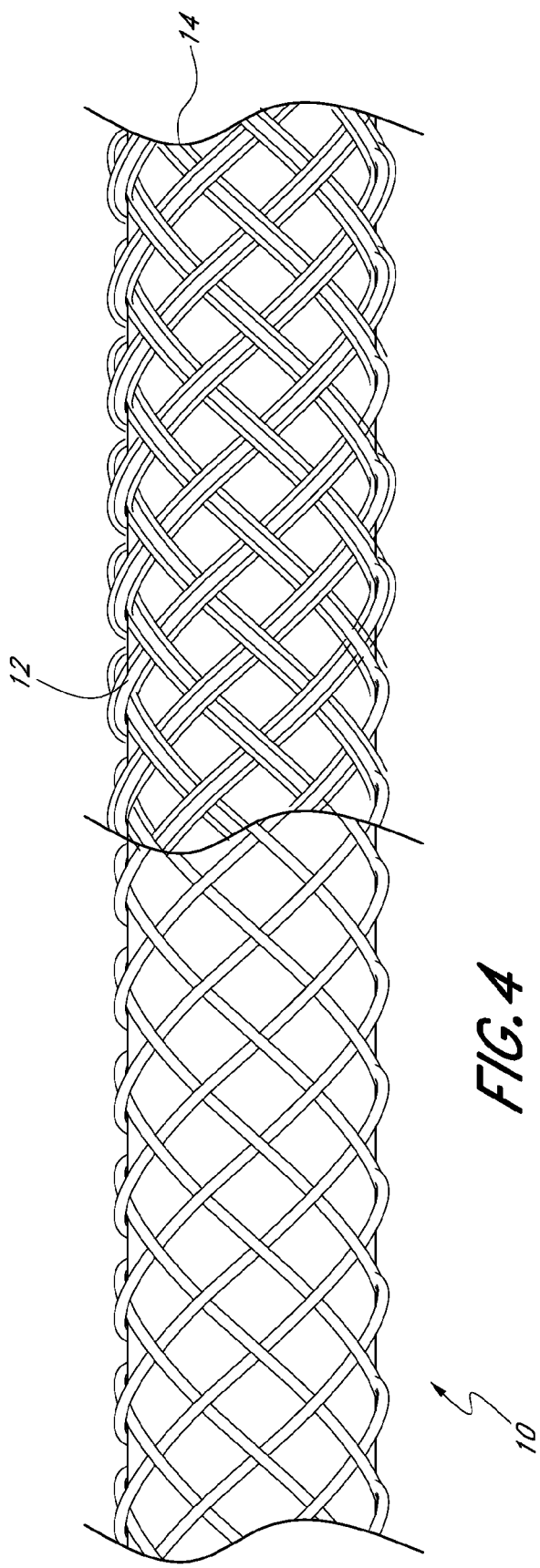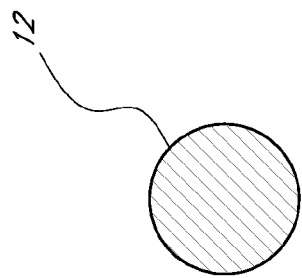
FIG.4
FIG.5

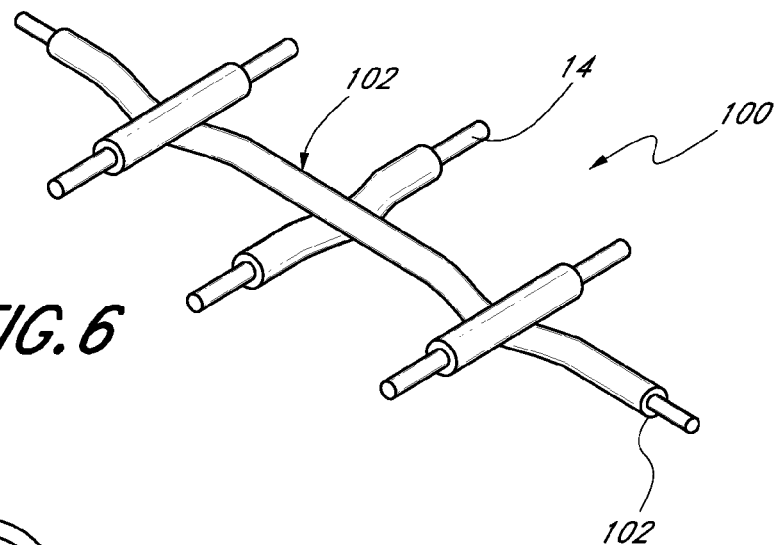
FIG.6
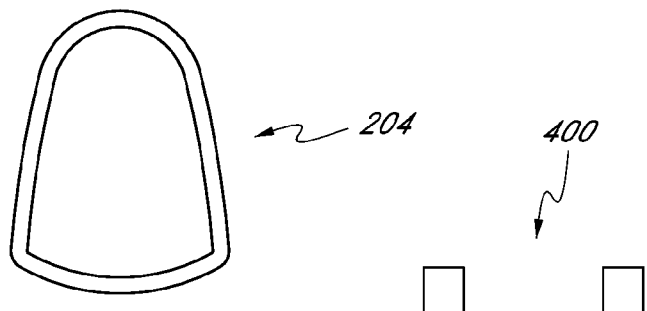
FIG.7
FIG.8
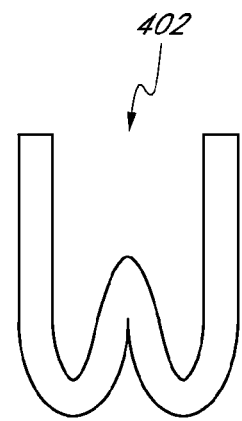
FIG.9
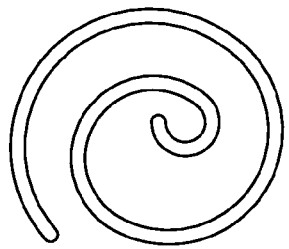
FIG.10
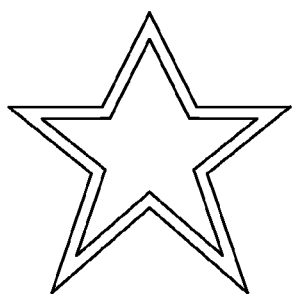
FIG.11

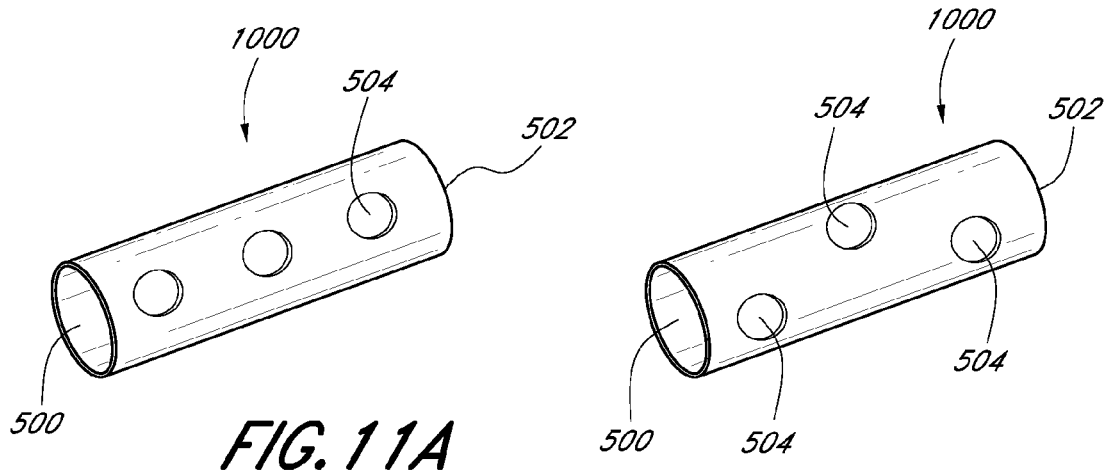
FIG. 11A
FIG. 11B
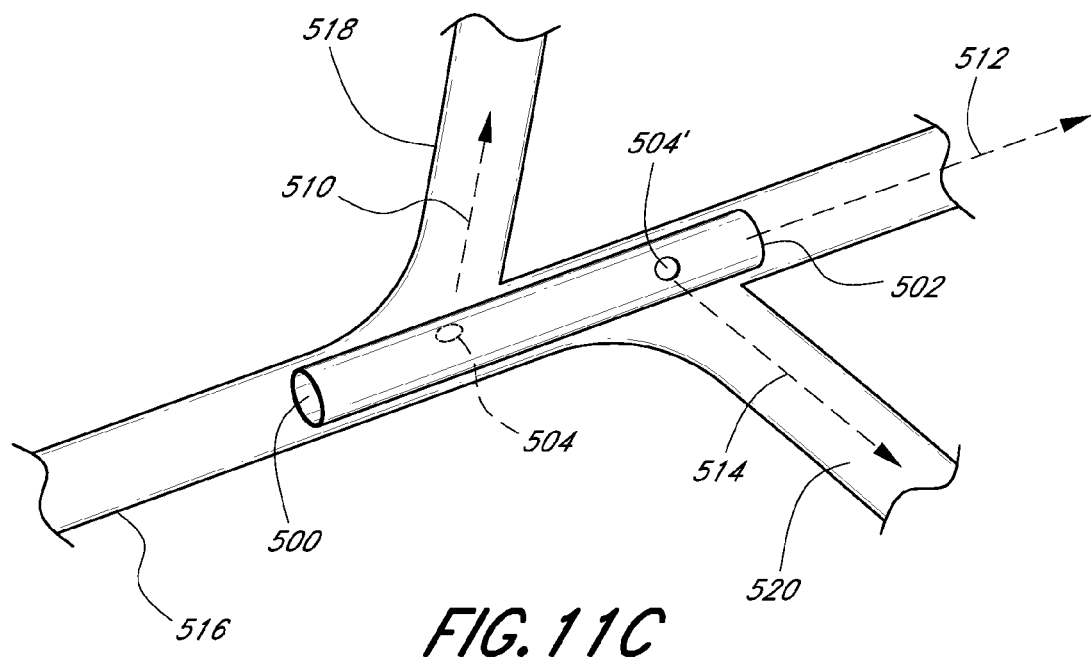
FIG. 11C

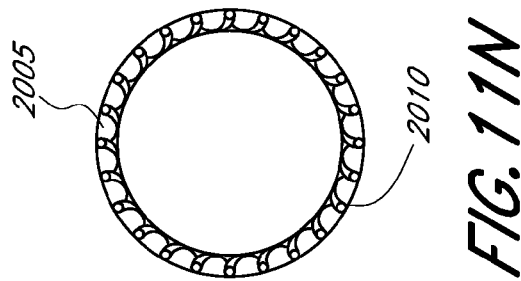
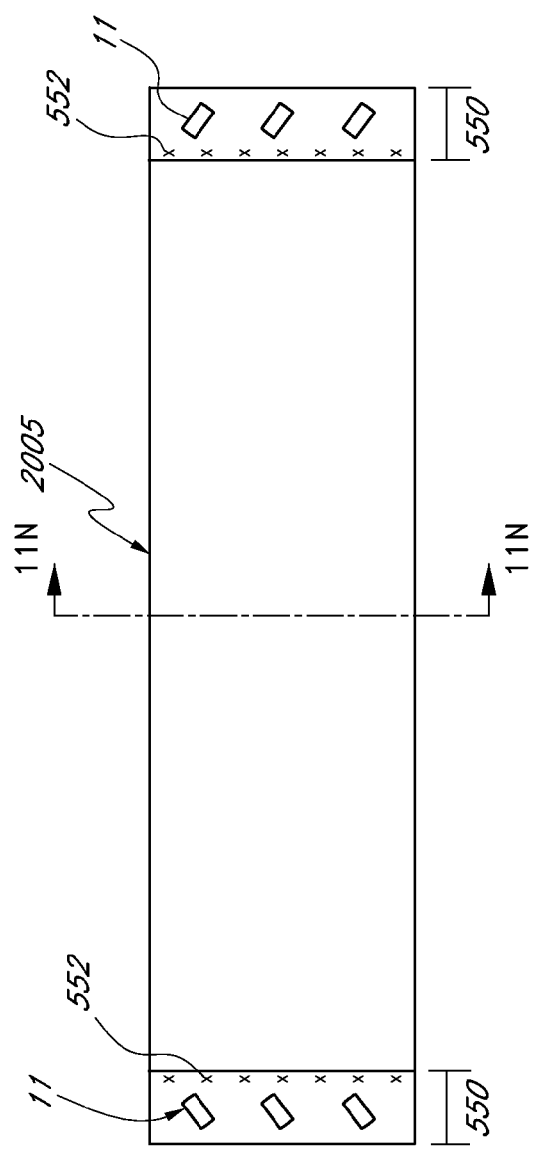

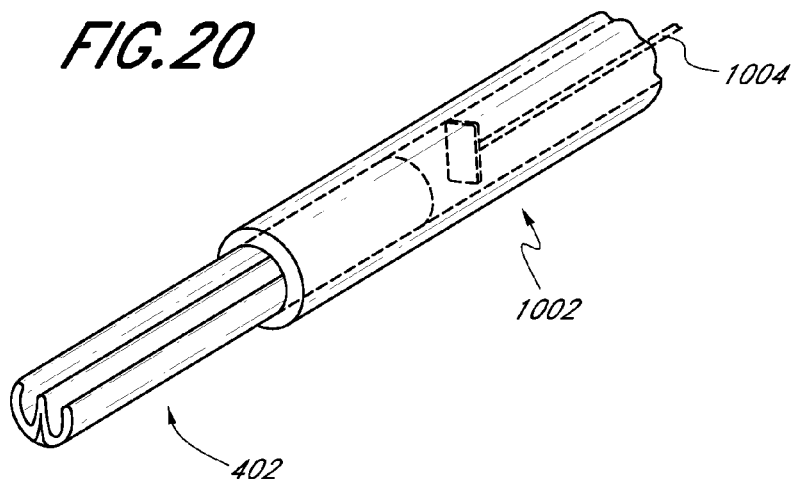

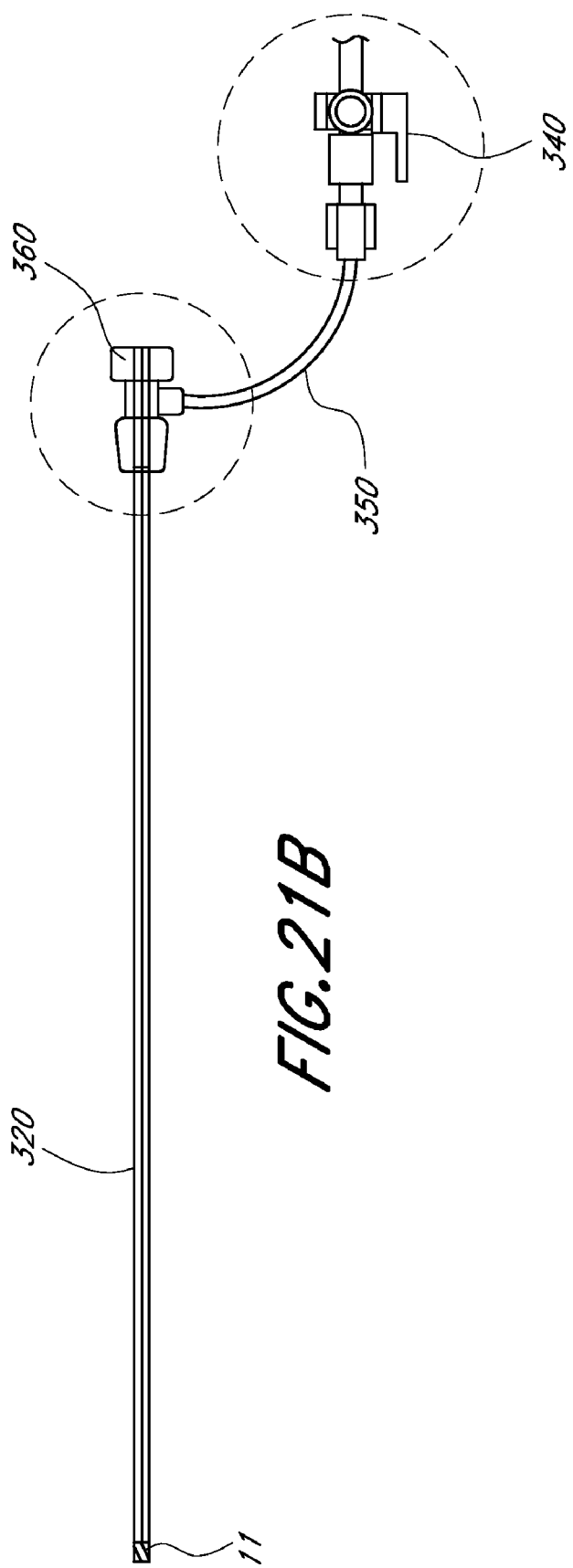

BIODEGRADABLE SELF-EXPANDING PROSTHESIS

This application claims priority under 35 U.S.C. §120 as a continuation-in-part application of U.S. patent application Ser. No. 11/972,406 filed on Jan. 10, 2008, and which is incorporated by reference in its entirety.

FIELD OF THE INVENTION

The present invention relates generally to implantable, radially expandable medical prostheses, often referred to as stents.

DESCRIPTION OF THE RELATED ART

The present invention relates generally to implantable, radially expandable medical prostheses which are frequently referred to as stents. In particular, some embodiments of the invention include a bioabsorbable self-expanding stent with a controlled-mass release and drug layer.

Atherosclerotic disease, for example, causes localized occlusion of the blood vessels resulting from the build-up of plaque. As the deposits increase in size, they reduce the diameter of the arteries and impede blood circulation.

Restenosis is the reclosure of a peripheral or coronary artery following trauma to that artery caused by efforts to open a stenosed portion of the artery, such as, for example, by balloon dilation, ablation, atherectomy or laser treatment of the artery. For these angioplasty procedures, restenosis occurs at a rate of about 20-50% depending on the definition, vessel location, lesion length and a number of other morphological and clinical variables. Restenosis is believed to be a natural healing reaction to the injury of the arterial wall that is caused by angioplasty procedures. The healing reaction begins with the thrombotic mechanism at the site of the injury. The final result of the complex steps of the healing process can be intimal hyperplasia, the uncontrolled migration and proliferation of medial smooth muscle cells, combined with their extracellular matrix production, until the artery is again stenosed or occluded.

Self-expanding medical prostheses frequently referred to as stents are well known and commercially available. They are; for example, disclosed generally in U.S. Pat. No. 4,655,771 to Wallsten, U.S. Pat. No. 5,061,275 to Wallsten et al., and Hachtmann et al., U.S. Pat. No. 5,645,559, which are all hereby incorporated by reference in their entirety. Devices are used within body vessels of humans for a variety of medical applications. Examples include intravascular stents for treating stenoses, stents for maintaining openings in the urinary, biliary, tracheobronchial, esophageal, and renal tracts, and vena cava filters.

A delivery device which retains the stent in its compressed state is used to deliver the stent to a treatment site through vessels in the body. The flexible nature and reduced radius of the compressed stent enables it to be delivered through relatively small and curved vessels. In percutaneous transluminal angioplasty, an implantable endoprosthesis is introduced through a small percutaneous puncture site, airway, or port and is passed through various body vessels to the treatment site. After the stent is positioned at the treatment site, the delivery device is actuated to release the stent, thereby allowing the stent to self-expand within the body vessel. The delivery device is then detached from the stent and removed from the patient. The stent remains in the vessel at the treatment site as an implant.

Stents must exhibit a relatively high degree of biocompatibility since they are implanted in the body. An endoprosthesis may be delivered into a body lumen on or within a surgical delivery system such as delivery devices shown in U.S. Pat. Nos. 4,954,126 and 5,026,377, which are hereby incorporated by reference in their entirety. Delivery devices that can be used for the present invention include U.S. Pat. Nos. 4,954,126 and 5,026,377, which are hereby incorporated by reference in their entirety. Suitable materials for use with such delivery devices are described in U.S. Pat. No. 6,042,578, hereby incorporated by reference in its entirety.

Commonly used materials for known stent filaments include Elgiloy® and Phynox® metal spring alloys. Other metallic materials than can be used for self-expanding stent filaments are 316 LVM stainless steel, MP35N alloy, and superelastic Nitinol nickel-titanium alloy including shape memory and temperature sensitive types. Another self-expanding stent, available from Schneider (USA) Inc. of Minneapolis, Minn., has a radiopaque clad composite structure such as shown in U.S. Pat. No. 5,630,840 to Mayer. Self-expanding stents can be made of a Titanium Alloy as described in U.S. Pat. No. 6,042,578, hereby incorporated by reference in its entirety.

The strength and modulus of elasticity of the filaments forming the stents are also important characteristics. Elgiloy®, Phynox®, MP35N and stainless steel are all high strength and high modulus metals. Nitinol has relatively low strength and modulus.

The implantation of an intraluminal stent will preferably cause a generally reduced amount of acute and chronic trauma to the luminal wall while performing its function. A stent that applies a gentle radial force against the wall and that is compliant and flexible with lumen movements is preferred for use in diseased, weakened, or brittle lumens. The stent will preferably be capable of withstanding radially occlusive pressure from tumors, plaque, and luminal recoil and remodeling.

Pharmacologic attempts have been made to reduce the rate of restenosis. These attempts have generally dealt with the systemic delivery of drugs via oral, intravascular, or intramuscular introduction. Little, if any success has been achieved with this systemic approach.

For drug delivery, it has been recognized for a long period of time that pills and injections may not be the best mode of administration. It is very difficult with these types of administration to obtain constant drug delivery. Patient noncompliance with instructions is also a problem. Through repeated doses, these drugs often cycle through concentration peaks and valleys, resulting in time periods of toxicity and ineffectiveness. Thus, localized drug treatment is warranted.

There remains a continuing need for self-expanding stents with particular characteristics for use in various medical indications. Stents are needed for implantation in an ever growing list of vessels in the body. Different physiological environments are encountered and it is recognized that there is no universally acceptable set of stent characteristics.

A need exists for a stent which has self expanding characteristics, but which is bioabsorbable, as well as a controlled-mass release and drug layer. A surgical implant such as a stent endoprosthesis is preferably made of a non-toxic, biocompatible material in order to minimize the foreign-body response of the host tissue. The implant also should have sufficient structural strength, biostability, size, and durability to withstand the conditions and confinement in a body lumen. Some important limitations of vascular stents, especially peripheral stents today include the high restenosis rate, even with drug-eluting stents. Possible non-limiting reasons for stent failure today include (1) continuous chronic over-expansion (excessive chronic outward forces leading to chronic injury), (2) strut fracture leading to uncovered areas and injury; (3) irreversible bending of the prosthesis as a consequence of excessive torsion forces; and (4) poor vascular conformability. A need exists for stents that improve on some or all of these limitations.

All documents cited herein, including the foregoing, are incorporated herein by reference in their entireties for all purposes.

SUMMARY OF THE INVENTION

There is provided in accordance with one aspect of the present invention, a hybrid biodegradable prosthesis. The prosthesis comprises a first end, a second end, and an elongate tubular body with a lumen therethrough. An outer layer comprises a drug delivery element. In one embodiment, the drug delivery element comprises polyphosphoester microspheres. The middle layer may comprise a plurality of flexible interbraided bioabsorbable filaments. An inner layer comprises a porous thermoplastic material. The inner layer provides a conduit for blood flow, and is configured to integrate into the vascular tissue. Thus, the prosthesis is a hybrid device, in which a first portion is absorbable or erodable over time, and a second portion is incorporated by cellular in-growth into the vascular intima.

In accordance with another aspect of the present invention there is provided a method of treating a patient. The method comprises the steps of providing a coaxial delivery system, including a catheter, loaded with a stent as described above. The catheter is advanced to a treatment site and the stent is deployed at the treatment site.

In accordance with a further aspect of the present invention, there is provided a medical system. This system comprises a catheter, having a radially expandable hybrid stent loaded thereon having an absorbable component and a permanent component.

An outer diameter at the first end of the prosthesis can be larger than a smaller outer diameter at a mid-point on the prosthesis axially displaced from the first end of the prosthesis. The larger diameter may be at least about 0.005 inches or more, or between about 5-9% greater in some embodiments than the smaller diameter. The outer layer may include any drug or biologically active substance depending on the desired clinical result, such as paclitaxel, rapamycin, zotarolimus, or tacrolimus.

The middle layer can be annealed to form various shapes and geometries. The bioabsorbable filaments can comprise a material selected from the group consisting of polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester; poly(amino acids), and poly(alpha-hydroxy acid). In some embodiments, the first end and/or the second end of the prosthesis comprise a drug delivery reservoir. In some embodiments, at least the first end or the second end of the stent is flared and folded to provide enhanced radial support. The stent may include at least one radioopaque marker element. The prosthesis can further include a second drug delivery element on an inner surface of the inner layer of the stent.

Also disclosed herein is a method of forming a vascular prosthesis, comprising: the steps of providing a first tubular body comprising a porous thermoplastic material; providing a second tubular body comprising a plurality of bioabsorbable filaments woven helically along a central axis of the second tubular body, the second tubular body having a outer diameter greater than that of the first tubular body; annealing the first tubular body to the second tubular body; and applying a coating layer to an outer surface of the second tubular body. In some embodiments, a crossing angle of the helically woven bioabsorbable filaments is between about 90 to 160 degrees, 120 and 160 degrees, or 90 to 140 degrees. In some embodiments, applying a coating layer involves one of spraying, dipping, or printing. The coating can be a drug coating.

Another aspect of the invention involves a biodegradable prosthesis, having a first end, a second end, and an elongate tubular body defining a sidewall with a lumen therethrough; a first layer comprising a set of flexible interbraided bioabsorbable filaments arranged in a helical pattern; and a second layer comprising a porous thermoplastic material, which can be ePTFE. The first layer and/or second layer can include folded portion(s) on a first end, such as a proximal end, and/or a second end, such as a distal end. The folded portions can be configured to remain folded while the prosthesis is implanted within a body lumen. The first layer could be either an outer or inner layer with respect to the second layer. The prosthesis could include 1, 2, 3, 4, 5, 6, or more radioopaque marker elements, which can be located anywhere on the prosthesis, such as secured within the folded layers of one or more folded portions of the prosthesis. The radioopaque marker element may be made of any appropriate metal or metallic material, such as a titanium-iridium alloy. The prosthesis can also include 1, 2, or more branch apertures disposed on the sidewall of the tubular body and configured to promote fluid flow into one or more side-branch vessels, such as at their ostia. In some embodiments, an outer diameter at the first end of the prosthesis is larger than an outer diameter at a mid-point on the prosthesis axially displaced from the first end of the prosthesis, such as at least 0.005 inches larger in some embodiments. The first layer and the second layer can be adhered, sutured, or otherwise attached together at various locations, such as within one or more folded portions of the prosthesis. A drug delivery characteristic, such as paclitaxel, rapamycin, zotarolimus, and tacrolimus for example can be operably attached to the first layer of the prosthesis in some embodiments. The first layer can be annealed to the second layer.

In another aspect, disclosed herein is an intraluminal prosthesis that has a first end, a second end, and an elongate tubular body within a lumen therethrough. The prosthesis can include a first layer with flexible interbraided filaments that can be helically woven in some cases. The first group of filaments can include a biodegradable material. The second group of filaments can comprise a metallic material. The prosthesis can include any number of filaments, such as between 10-36 filaments in some embodiments. The filaments that include a metallic material can include no more than about 70%, 60%, 50%, 40%, 30%, 25%, 20%, 10% or less of the total number of filaments. A second layer of a porous thermoplastic material can be operably attached to the first layer, as either an outer layer or an inner layer with respect to the first layer.

A method of forming a vascular prosthesis is also disclosed, including the steps of providing a first tubular body comprising a porous thermoplastic material; providing a second tubular body comprising a plurality of bioabsorbable filaments woven helically along a central axis of the second tubular body; folding a portion of the first tubular body over a portion of the second tubular body; and annealing the first tubular body to the second tubular body. The method can also include the step of applying a coating layer to an outer surface of the second tubular body. The crossing angle of the helically woven bioabsorbable filaments can be from about 90 to about 140 degrees in some embodiments. Applying a coating layer, such as a drug coating can involve spraying, dipping, or microprinting.

In another embodiment, a method of treating a patient can include providing a coaxial delivery system, including a catheter loaded with a prosthesis as disclosed elsewhere herein, and deploying the prosthesis in the patient at a treatment site. In some embodiments, the coaxial delivery system is configured to house multiple stents for delivery during a single procedure, such as at least 2, 3, 4, 5, or more stents.

Also disclosed herein is a medical system that includes a catheter and a radially expandable stent as described elsewhere herein, carried by a distal section of the catheter. The system can also include a lubricious coating on the catheter.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 1 schematically illustrates in partial cut away view various sections of a multilayer self-expanding prosthesis according to one embodiment of the invention.

FIG. 2A illustrates a stent with enlarged, flared, tapered proximal and distal ends, according to one embodiment of the invention.

FIG. 2B is a close-up side view of a cross-section of the stent ends shown of FIG. 2A that illustrates flared ends of the stent. The inner synthetic membrane layer may be compressed, laminated, and/or bonded to the braided bioabsorbable layer, such as through induction of heat and compression.

FIG. 2C schematically illustrates a plurality of tubular bodies in which layers 2010 and 2030 can be annealed together to create a stent, according to one embodiment of the invention. Layer 2020 can also be created by spraying, dipping, and/or micro-printing coating processes.

FIGS. 3-4 illustrates in intermediate stent layer with biodegradable interwound filaments, which can provide increased radial support for the stent, according to one embodiment of the invention.

FIG. 5 illustrates a cross-section of a polymeric filament.

FIG. 6 illustrates a schematic cut-away view of a woven filament layer with a coated drug-release layer, according to one embodiment of the invention.

FIG. 7 illustrates a stent with a non-circular acorn-shaped cross-section, according to one embodiment of the invention.

FIGS. 8-11 illustrate various folded stent configurations, according to some embodiments of the invention.

FIGS. 11A-11B illustrate a schematic perspective view of a stent having one, two, or more branch apertures, in accordance with some embodiments of the invention.

FIG. 11C illustrates a schematic perspective view of a stent having side orifices implanted in a main vessel with the side orifices providing a flow path into side vessels, in accordance with one embodiment of the invention.

FIG. 11M is a schematic view of a stent having an inner biodegradable woven layer and an outer porous membrane layer, according to one embodiment of the invention.

FIG. 11N is a cross-sectional view of the stent of FIG. 11M through line 11N-11N.

FIGS. 12-20 illustrate various devices for delivery of a stent to a body lumen, according to some embodiments of the invention.

FIGS. 21A-21C illustrate an alternative stent delivery system and various components, according to some embodiments of the invention.

DETAILED DESCRIPTION OF THE PREFERRED EMBODIMENT

Figure 11D:
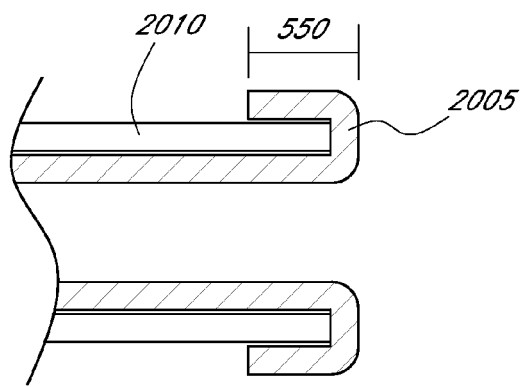
FIGS. 11D-11F illustrate cross-sectional views of various folding patterns of one or more layers of a stent, in accordance with some embodiments of the invention.

The present invention relates generally to a hybrid construct adapted for implantation in a living organism, such as a human. The construct includes at least a first portion which is bioabsorbable, and may support a drug delivery characteristic. The bioabsorbable component may be attached to a non-absorbable or permanent component. Thus, following implantation in the body, the bioabsorbable component gradually disappears, while the permanent component becomes attached to and/or integrated within the adjacent tissue. The term 'bioabsorbable' is used herein only to indicate a transient presence in the body, and to include all mechanisms by which the implant or implant component may disappear over time, including dissolution, absorption, erosion or others.

The hybrid construct of the present invention will be described primarily herein in a tubular form, particularly adapted for implantation within the cardiovascular system. It should be appreciated that the tubular form of the present invention may also be configured for implantation within other hollow organs or tubular structures within the body, such as the gastro intestinal tract including the stomach, esophagus, various portions of the intestine and colon. The tubular construct may alternatively be configured for positioning in the airways, such as the trachea, bronchial tubes, or other portions of the lung, and the sinus and nasal cavities. Alternative embodiments may be configured for implantation within the urethra, ureters, fallopian tubes, uterus, vagina, or elsewhere as will be appreciated by those of skill in the art. Within the cardiovascular system, tubular embodiments of the present invention may be configured for implantation within the coronary vasculature, peripheral vasculature, and intracranial vasculature. Additional indications will be discussed below.

Nontubular embodiments of the present invention may be provided in the form of a multilayer patch, which may be utilized to span or repair any of a variety of tissue defects, such as hernias, ulcerations, perforations, or other defects or injuries caused by surgery, traumatic injury or disease states.

For example, the embodiment illustrated in FIG. 1 comprises at least three layers formed in a tubular configuration for intravascular implantation. Although described below as discrete layers, it should be appreciated that the composition of each of the three layers may be interwoven or intermingled with the adjacent layer or layers as will be appreciated by those of skill in the art in view of the description herein.

Referring to FIG. 1, a structural intermediate support layer 201 may comprise a woven braided helically wound or otherwise configured fabric or filament structure. The filament layer 201 may be absorbable as is disclosed elsewhere herein. Preferably, the filament layer 201 is self-expandable from a reduced cross-sectional configuration such as for transluminal navigation to a deployment site, to an enlarged cross-sectional configuration such as for lining a vessel. The filament layer 201 is sometimes referred to herein as the second or intermediate layer.

Disposed concentrically within the central lumen defined by the second layer 201 is an inner first layer 200. The inner first layer 200 comprises a thin membrane discussed in greater detail below. In certain embodiments, the membrane is provided with a microporous or macroporous structure configured to permit cellular in-growth from the adjacent vascular wall, optimally of a nature sufficient to provide a viable neointimal lining on the inner, luminal surface of the implant.

The outermost or third layer 202 comprises a drug release characteristic. The drug release characteristic may be provided in any of a variety of ways, such as by inclusion of microspheres on the surface of the construct, dipping, spraying or other coating operations, chemical and/or mechanical binder layers or tie layers or the like. The outer layer 202 may thus reside within the interstitial spaces between the adjacent filaments of the second layer 201 and/or radially outwardly disposed with respect to the filaments of the second layer 201. Alternatively, the outer layer 202 may comprise a coating upon each individual filament, as is discussed below.

In general terms, the construct of the present invention is intended to be transvascularly advanced to a treatment site and deployed such that the outer layer 202 is brought into contact with the intimal lining of the vessel, through the self-expanding characteristic created by the second layer 201 and potentially assisted by the first layer 200. This permits blood flow through the central lumen, while the drug delivery layer is maintained against the vessel wall. The construct remains in position while drug is eluted from the outer layer 202. In an absorbable embodiment, at least a first portion of the stent which may include the second layer 201 and an outer layer 202 may be absorbable or erodable at the implantation site. At the same time, the intermediate tubular layer 200 may be non-erodable. In this embodiment, after a desired predetermined period of time, the implant ceases to deliver drug from the outer layer 202, the second layer 201 and outer layer 202 gradually are absorbed by the body, and cellular in-growth from the vessel wall enters the porous structure of the first layer 200, to provide a robust cellular lining on the luminal surface of the first layer 200. In this manner, the tubular layer 200 is integrated into the vessel wall and thus becomes biologically "invisible" to blood flow through the vessel.

FIG. 1 schematically illustrates in a partial cut-away view various sections of an embodiment of a self-expanding multilayer prosthesis 1000, or stent that is preferably at least partially bioresorbable in some embodiments. The prosthesis 1000 comprises multiple layers. A first layer 200 which is preferably the innermost layer, can be a membrane made of a biocompatible material such polyethylene, polyurethane, Teflon, or ePTFE with a thickness of about 0.001 to 0.010 inches, preferably between about 0.002 to 0.005 inches, and an inside diameter of between about 0.20 to 0.57 inches, such as about 0.267 +/−0.005 inches in some embodiments. The first layer 200 is preferably porous (e.g., via pores 101), having a pore size of between about 0.05-1.5 microns, such as between about 0.05 to 1 microns, or between about 0.1 and 0.5 microns in some embodiments. Porous as used herein includes tortuous pathways such as is present in the fibril and node structure of ePTFE. The average internodal distance could be between about 15-60 micrometers in some embodiments, such as between about 30-50 micrometers. The porosity could be, for example, between about 10-99%, such as between about 50-95% or about 80-90% in some embodiments. In some embodiments, the water entry pressure of the layer could be between about 5-15 psi, such as between about 6.5-9 psi. In some embodiments, the machine direction tensile strength of the layer could be at least about 1,000 psi, 2,000 psi, 4,000 psi, or more, with a transverse direction tensile strength of at least about 1,000 psi, 1,500 psi, 1,650 psi, 1,800 psi, 2,000 psi, or more. The biocompatible membranous layer 200 can be, in some embodiments, interwoven radially to a second layer 201 of bioabsorbable helically wound polymeric filaments 14, for example, polylactic acid-polyethylene oxide copolymers, polydioxanone, polyglycolic acid, polylactic acid, polycaprolactone, polycarolactone, polygluconate, polyanhyride, polyaminoacids, and combinations thereof, as discussed in greater detail below.

The outer layer 202 preferably comprises a controlled drug release element 102, which may be incorporated into polyphosphate ester microspheres deposited on layer 201 in some embodiments. In some embodiments, the controlled drug release element layer may be deposited on either or both of the inner and outer surfaces of the biocompatible layer 200 and/or the polymeric filament layer 201. The drug may be any drug known in the art. In some embodiments, the drug is an immunosuppressant or antiproliferative agent, such as paclitaxel (Taxol), rapamycin (Sirolimus), zotarolimus, or tacrolimus. In other embodiments, the drug may be an anti-platelet agent such as heparin, hirudin, or enoxaparin, or any other drug or bioactive compound depending on the desired clinical result.

Stent 1000 may also include one or more radioopaque marker elements 11 as discussed in greater detail below.

To satisfy the clinical needs on drug-eluting stents, in terms of providing the effective concentration of bioactive active agents in a timely manner, some embodiments provide one or more pharmaceutical agents which can be highly efficacious in controlling virtually all the biological events leading to restenosis.

In some embodiments, the prosthesis has a cambered interior surface of between about 10 to 20 degrees, similar to that disclosed in U.S. Pat. No. 5,551,954 to Buscemi et al, which is hereby incorporated by reference in its entirety.

Controlled release of a drug, via, for example, a bioabsorbable polymer offers to maintain the drug level within the desired therapeutic range for the duration of the treatment. In the case of stents, the prosthesis materials will maintain vessel support for weeks, months, or more or until incorporated into the vessel wall even with bioabsorbable, biodegradable polymer constructions. While the drug release layer is depicted as the outermost layer, it can be alternatively present as an inner or intermediate layer. In some embodiments, multiple drug release layers may be present.

Several polymeric compounds that are known to be bioabsorbable and hypothetically have the ability to be drug impregnated may be useful in prosthesis formation herein. These compounds include: poly-1-lactic acid/polyglycolic acid, polyanhydride, and polyphosphate ester. A brief description of each is given below.

Poly-1-lactic acid/polyglycolic acid has been used for many years in the area of bioabsorbable sutures. It is currently available in many forms, i.e., crystals, fibers, blocks, plates, etc. These compounds degrade into non-toxic lactic and glycolic acids.

Another compound which could be used are the polyanhydrides. They are currently being used with several chemotherapy drugs for the treatment of cancerous tumors. These drugs are compounded into the polymer which is molded into a cube-like structure and surgically implanted at the tumor site.

In some embodiments, the drug delivery element includes a polyphosphate ester. Polyphosphate ester is a compound such as that disclosed in U.S. Pat. Nos. 5,176,907; 5,194,581; and 5,656,765 issued to Leong which are incorporated herein by reference in their entirety. Similar to the polyanhydrides, polyphosphate ester is suitable for drug delivery. Unlike the polyanhydrides, the polyphosphate esters have high molecular weights (600,000 MW average), yielding attractive mechanical properties. This high molecular weight leads to transparency, and film and fiber properties. It has also been observed that the phosphorous-carbon-oxygen plasticizing effect, which lowers the glass transition temperature, makes the polymer desirable for fabrication. The highly hydrolytically reactive phosphorous ester bond, the favorable physical properties, and the versatile chemical structure make the polyphosphate esters a superior drug delivery system for a prosthesis. PPE microspheres may also be incorporated into the stent as disclosed in U.S. Pat. No. 5,545,208 to Wolff et al., which is hereby incorporated by reference in its entirety.

The drug-eluting layer may be operably attached to the other layers of the prosthesis, for example, by spray-dipping, coating, annealing, or covalently or noncovalent binding as known in the art.

Non-limiting examples of drugs that may be incorporated into the prosthesis described herein that can be used individually or in different combinations are discussed below.

Paclitaxel, is an antineoplastic compound which is used clinically in commercially available drug-eluting stents. This drug can also be used as an anti-inflammatory agent with an exceptionally narrow therapeutic window beyond which it can be cytotoxic. In some embodiments, the prosthesis may include one drug delivery reservoir with paclitaxel and another drug delivery reservoir with an antineoplastic agent, sometimes in combination with other drugs known for their anti-inflammatory activities (e.g., naproxen) and/or being immunosuppressant (e.g., rapamycin).

Rapamycin is clinically used in commercially available drug-eluting stents. This drug is also used as an immunosuppressant having a wide therapeutic window. However, its use in drug-eluting stents in the prior art may not provide the optimum pharmacokinetics when released from a non-uniform coating. This invention also provides for use of rapamycin in combination with at least one additional bioactive agent, with different pharmacological activity, such as in one or more drug delivery reservoirs. Typical examples of these other agents include endothelial cell growth promoters (e.g., vascular endothelial growth factor or its polypeptide functional analog), smooth muscle growth inhibitors, and antibiotics.

Antineoplastic agents, such as dactimycin, doxorubicin, mitomycin, mitoxantrone, and topotecan, also exhibit antibiotic activities. These can be used individually or in combination with other drugs (that may be loaded in separate drug delivery reservoirs), particularly those known to exhibit anti-inflammatory activity and/or promote endothelial cell growth.

Antineoplastic agents are also folate antagonists, such as methotrexate. The latter drug is also antimetabolite and immunosuppressant but can be an irritant. To mediate the latter effect, methotrexate can be used in combination with an anti-inflammatory drug and/or endothelial cell growth promoters, such as vascular endothelial growth factor (VEGF) or its polypeptide functional analog.

Anti-inflammatory drugs, which can be used alone or in combination with antineoplastic agents and/or immunosuppressants. Examples of these anti-inflammatory drugs include (a) colchicine, which is also an antineoplastic compound that can be used to retard smooth muscle cell proliferation and can preferably be used in combination with an endothelial cell growth promoter, such as VEGF or its polypeptide functional analog; (b) the NSAID, indomethacin; (c) the NSAID, piroxicam, which may also be an immunosuppressant; and (d) the corticosteroid, prednisone, which may also exhibit antineoplastic activity.

Leflunamide, a member of the isoxazole class of drugs, exhibits anti-inflammatory, antiproliferative, and immunosuppressive activities. This can be used alone or in combination with an endothelial cell promoter.

Thalidomide is an anti-inflammatory drug that also exhibits anti-angiogenic and immunosuppressive activities. This can be used alone or in combination with an endothelial cell growth promoter.

Curcumin is an anti-inflammatory drug, which also exhibits antiproliferative activities.

Mycophenolate mofetil is an immunosuppressant that is endowed with anti-inflammatory properties. This can be used alone or in combination with an endothelial cell promoter.

Methotrexate is an anti-inflammatory and immuno-regulatory drug. It exhibits antiproliferative activity and can be used alone or in combination with an endothelial cell growth promoter, such as vascular endothelial growth factor or its polypeptide functional analog.

Dihydrofolate reductase is an anti-infective, antineoplastic, and anti-inflammatory agent. It can be used alone or in combination with an endothelial cell growth promoter.

Deferoxamine has been used extensively as chelation therapy in iron-loaded states and noted recently for its usefulness as an antiproliferative, anti-inflammatory, and immunosuppressive agent. It can be used alone or in combination with an endothelial cell growth promoter.

Antibiotics produced by members of the bacterial genus Streptomyces, such as streptomycin-B, actinomycin-F1, and actinomycin-D, also exhibit antineoplastic and/or immunosuppressive activities.

Antineoplastics which are also antimetabolites, such as fludarabine and fluorouracil, can be used alone or in combination with an anti-inflammatory drug.

Growth factors such as endothelial or fibrous tissue growth factors, agonists or antagonists, or neurotrophic proteins, such as nerve growth factor, can also be incorporated.

In some embodiments, tropomyosin along with troponin could be utilized to regulate the shortening of the muscle protein filaments action and myosin. In resting muscle fibers, tropomyosin is displaced from its normal binding groove by troponin.

In some embodiments regenerative cells such as adult stem cells, vascular endothelial cells, vascular smooth cells including but not limited to myofibril including RNA(MIR) promotes cardiac myofibril gene expression and is important for embryonic heart development. Other similar stem cells such as human embryonic stem cells from Geron (Menlo Park, Calif.) can also be operably attached to one or more layers of the stent.

In some embodiments, the controlled drug release element comprises polyphosphoester microspheres. Layers 200 and 201 of FIG. 1, in some embodiments, can be configured with a certain porosity meeting the Association for the Advancement of Medical Instrumentation (AAMI) standard for vascular graft applications to allow the device to integrate into tissue at the vascular site. This feature would improve lodging within the vessels, as well as promotion of integration and cell growth through the sidewall of the permanent component(s) of the implant to embed the implant in the vascular wall at the treatment site.

FIG. 2A illustrates an embodiment of a prosthesis 108, shown schematically and not to scale, with enlarged, flared end portions 9. The outer drug delivery element and inner tubular membrane are not shown for clarity. The enlarged end portions 9 are created as the ends of fibers 12 from the biodegradable polymer layer (discussed below) running axially across the prosthesis 108 are secured at the distal and proximal end of the prosthesis at 9. As will be discussed, in some embodiments, fibers 12 can be interwoven in an over and under braided configuration intersecting at points such as 14 to form an open mesh or weave construction. The added thickness created by the laminated and/or bonded secured and folded fibers 12 at both ends of the device can be utilized as a platform to create expanded drug delivery reservoirs for one or more drugs at the distal and proximal end of the device, to provide directional drug delivery as well as controlled drug release through surfaces of inner member and/or on the surfaces of the exterior of the outer member (e.g., the drug coating). The fiber ends 9 also provide increased radial support at both ends of the device. The enlarged lateral ends 9 can result in a flared, expanded cross-section 111 as shown in FIG. 2B. When fully deployed, in some embodiments, the inner luminal diameter of the prosthesis is substantially consistent in diameter throughout its length and generally annular shaped, the outer diameter of copolymer layer at the distal and/or proximal end of the device D2 at the expanded state is larger by 0.002 to 0.010 inches, or 0.005 to 0.010 inches in some embodiments larger than the outer diameter at a midportion of the device D1, creating one or more drug delivery reservoirs for one or more types of drugs. Alternatively, the drug delivery element may be present not only at the ends but extending partially or completely over the prosthesis.

The stent 108 illustrated in FIG. 2A has in its unconstrained, expanded state a first outer cross-sectional diameter D2 at each end and a second, smaller cross-sectional diameter D1 at the central apex portion of the stent. The cross-sectional diameter of the stent preferably decreases from one end to a central apex portion, and preferably increases from the central apex portion to the second end. The larger cross-sectional diameter D2 at the ends relative to the central apex portion diameter D1 advantageously provides increased radial support for the stent at the first and second ends. In some embodiments, the ratio of D2/D1 is at least about 1.005, 1.01, 1.02, 1.03, 1.04, 1.05, 1.07, 1.10, 1.15, 1.20, 1.25, 1.30, or more.

In some embodiments, the prosthesis is selected to be oversized by at least about 3%, 4%, 5%, 6%, 7%, 8%, 9%, 10%, or more than the diameter of the body lumen that the prosthesis is inserted into, or between about 3% and 10% in some embodiments.

While the prosthesis 108 shown in FIG. 2A has a variable outer diameter, the prosthesis 108 preferably has relatively constant inner diameter throughout its axial length to provide a stable flow path when the prosthesis is placed within a blood vessel.

FIG. 2C illustrates schematically an exploded view of a first tubular body 2005 that may be made of a porous biocompatible material such as ePTFE, PTFE, polyurethane, or similar materials. The second tubular body 2010 comprises a helically wound and or braided polymer that can optionally include a polyphosphoester or other drug coating 2020. A stent may be formed in some embodiments by annealing (e.g., on a mandrel) the first 2005 and second 2010 tubular bodies. The first tubular body 2005 preferably has a smaller diameter than the second tubular body 2010 such that the first tubular body 2005 becomes the inner layer and the second tubular body 2010 becomes the intermediate or outer layer. In some embodiments, a third tubular body 2020 comprising a drug delivery layer may also be present and can be annealed to the second tubular body 2010, or applied on via a coating, spraying or dipping process to form a tri-layer stent.

Biodegradable Layer

The biodegradable intermediate layer may include a biodegradable polymeric material, such as described in U.S. Patent Publication No. 2006/0129222 A1 to Stinson, hereby incorporated by reference in its entirety.

In some embodiments, a blended combination of polymer such as DLPLA-poly(di-lactide) can be utilized. DLPLA is an amorphous polymer exhibiting a random distribution of both isomeric forms of lactic acid, and accordingly is unable to arrange into an organized crystalline structure. This material has lower tensile strength, higher elongation, and a much more rapid degradation time, making it more attractive as a drug delivery system. Poly(1-lactide) is about 37% crystalline, with a melting point of 170-180° C. and a glass-transition temperature of 60-69° C. The degradation time of LPLA is much slower than that of DLPLA, requiring more than 2 years to be completely absorbed. Copolymers of l-lactide and dl-lactide have been prepared to disrupt the crystallinity of l-lactide and accelerate the degradation process.

PGA-polyglycolide is the simplest linear aliphatic polyester. PGA was used to develop the first total synthetic absorbable suture, marketed as Dexon in the 1960's by Davis and Geck Inc. (Danbury, Conn.) Glycolide monomer is synthesized from the dimerization of glycolic acid. Ring-opening polymerization yields high-molecular-weight materials, with approximately 1-3% residual monomer present PGA is highly crystalline (45-55%), with a high melting point (200-225° C., such as 200-210° C.) and a glass-transition temperature of 35-40° C. Because of its high degree of crystallization, it is not soluble in most organic solvents; the exceptions are highly fluorinated organics such as hexafluoroisopropanol. Fibers from PGA exhibit high strength and modulus and are too stiff to be used as sutures except in the form of braided material. Sutures of PGA lose about 50% of their strength after 2 weeks and 100% at 4 weeks, and are completely absorbed in 4-6 months. Glycolide has been copolymerized with other monomers to reduce the stiffness of the resulting fibers.

Lactide is the cyclic dimer of lactic acid that exists as two optical isomers, d and l. l-lactide is the naturally occurring isomer, and dl-lactide is the synthetic blend of d-lactide and l-lactide. The homopolymer of l-lactide (LPLA) is a semi crystalline polymer. These types of materials exhibit high tensile strength and low elongation, and consequently have a high modulus that makes them more suitable for load-bearing applications such as in orthopedic fixation and sutures. Poly (dl-lactide) (DLPLA) is an amorphous polymer exhibiting a random distribution of both isomeric forms of lactic acid, and accordingly is unable to arrange into an organized crystalline structure. This material has lower tensile strength, higher elongation, and a much more rapid degradation time, making it more attractive as a drug delivery system. Poly(1-lactide) is about 37% crystalline, with a melting point of 175-178° C. and a glass-transition temperature of 60-65° C. The degradation time of LPLA is much slower than that of DLPLA, requiring more than 2 years to be completely absorbed. Copolymers of l-lactide and dl-lactide have been prepared to disrupt the crystalline of l-lactide and accelerate the degradation process.

Mechanical properties generally increase with increasing molecular weight. For instance, the strength and modulus of PLA generally increases with increasing molecular weight. Degradation time generally decreases with decreasing initial molecular weight (i.e., a stent made of a low molecular weight polymer would be bioabsorbed before a stent made of a high molecular weight polymer). Low molecular weight PLA is generally more susceptible to thermo-oxidative degradation than high molecular weight grades, so an optimum molecular weight range should be selected to balance properties, degradation time, and stability. The molecular weight and mechanical properties of the material generally decreases as degradation progresses. PLA generally has a degradation time greater than 1 year. PLA has a glass transition temperature of about 60° C., so care must be taken not to store products in environments where high temperature exposure may result in dimensional distortion.

PLA, PLLA, PDLA and PGA include tensile strengths of from about 40 thousands of pounds per square inch (psi) to about 120 psi; a tensile strength of 80 psi is typical; and a preferred tensile strength of from about 60 psi to about 120 psi. Polydioxanone, polycaprolactone, and polygluconate include tensile strengths of from about 15 psi to about 60 psi; a tensile strength of 35 psi is typical; and a preferred tensile strength of from about 25 psi to about 45 psi.

PLA, PLLA, PDLA and PGA include tensile modulus of from about 400,000 pounds per square inch (psi) to about 2,000,000 psi; a tensile modulus of 900,000 psi is typical; and a preferred tensile modulus of from about 700,000 psi to about 1,200,000 psi. Polydioxanone, polycaprolactone, and polygluconate include tensile modulus of from about 200,000 psi to about 700,000 psi; a tensile modulus of 450,000 psi is typical; and a preferred tensile modulus of from about 350,000 psi to about 550,000 psi.

PLLA filament has a much lower tensile strength and tensile modulus than, for example, Elgiloy® metal alloy wire which may be used to make braided stents. The tensile strength of PLLA is about 22% of the tensile strength of Elgiloy®. The tensile modulus of PLLA is about 3% of the tensile modulus of Elgiloy®. Stent mechanical properties and self-expansion are directly proportional to tensile modulus of the material. As a result, a PLLA filament braided stent made to the same design as the metal stent has low mechanical properties and would not be functional. The invention advantageously provides polymeric braided stents with radial strength similar to metal stents and the required mechanical properties capable of bracing open endoluminal strictures.

A bioabsorbable PLLA braided tubular stent changes size when constrained onto a catheter delivery system and when deployed. A deployed PLLA stent is generally longer in length and smaller in diameter than a PLLA stent prior to loading. For example, PLLA stents that were initially 30 mm long with external diameters of about 10.7 mm had deployed lengths of about 90 mm with diameters of about 6.3 mm.

Self-expanding stents can be formed from a number of resilient filaments which are helically wound and interwoven in a braided configuration. The stents assume a substantially tubular form in their unloaded or expanded state when they are not subjected to external forces. When subjected to inwardly directed radial forces the stents are forced into a reduced-radius and extended-length loaded or compressed state. The stents are generally characterized by a longitudinal shortening upon radial expansion.

In one preferred embodiment, the device is a stent which includes a plurality of elongate polylactide bioabsorbable polymer filaments, helically wound and interwoven in a braided configuration to form a tube. Bioabsorbable implantable endoprostheses such as stents, stent-grafts, grafts, filters, occlusive devices, and valves may be made of poly(alpha-hydroxy acid) such as poly-L-lactide (PLLA); poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino-acids), or related copolymers materials, each of which have a characteristic degradation rate in the body. For example, PGA and polydioxanone are relatively fast-bioabsorbing materials (weeks to months) and PLA and polycaprolactone are a relatively slow-bioabsorbing material (months to years).

A stent constructed of a bioabsorbable polymer provides certain advantages relative to metal stents such as natural decomposition into non-toxic chemical species over a period of time. Also, bioabsorbable polymeric stents may be manufactured at relatively low manufacturing costs since vacuum heat treatment and chemical cleaning commonly used in metal stent manufacturing are not required. Furthermore, such stents could be advantageous when two, three, or more stents are overlapped together in avoiding or reducing wear damage and crevice corrosion that may occur with overlapped metallic stents.

In comparison, a metal self-expanding stent generally has about the same dimensions before loading and after deployment. For metal stents, if it is known that the patient has a 9 mm diameter vessel, then a 10 mm metal stent (stent is intentionally oversized by about 1 mm) is loaded onto the delivery system for implantation. This rule is not applicable for a polymer stent because more oversizing is necessary.

PLLA-Poly (L-lactic acid) fibers are processed by a two step melt-spinning method (extrusion and hot draw) from PLLA with three different Viscosities -average molecular weight of approximately (494,000 g/mol, 305,000 g/mol, and 262,000 g/mol). Before spinning, the polymer flakes are first milled into powders and dried under vacuum. The extrusion die is operated at a temperature of 200° C.±30° C. In some embodiments, depending on the diameter of fiber utilized, up to 38-spindle braiders/winders may be required for manufacturing.

The outer layer surface structure can vary from particle beads texture for enhanced lodging to fibrous materials. The fiber manufacturing process in some embodiments includes a melt extrusion immediately followed by a drawing process to create a self-reinforced embodiment. To attain maximum radial strength for the device the drawing of the molten referenced materials can occur, e.g., at an angle ranging from 60° to 140° degrees. The isotropic polymer is transformed into a highly anisotropic self-reinforced configuration. The self-reinforced fiber has a high degree of molecular orientation in the direction of the long axis of the fiber. The vacuum dried material is extruded by an industrial grade extruder having a 1.0 mm monofilament die. In the drawing process, the materials could be oriented with draw ratios of approximately 6.0 to 10.0, corresponding to a final diameter of 0.029 mm in some embodiments. The self reinforced fibers are braided into a cylindrical/tubular shape onto a 4-16 mm mandrel, the porous layer, or a cast using two vertically operating 24-spindle braiding/winding machines. Heat treatment takes place in the vacuum oven at 120-160° C. for 7-25 minutes, or at up to 200° C. for between 15-35 minutes in some embodiments. Next the stents are left in at room temperature for approximately 15 to 25 minutes. The viscosity-average molecular weight, in some embodiments, can be approximately 220,000 g/mol after extrusion. The drawing processes decrease the viscosity average weight to about 48,000 g/mol.

The mandrel's outer diameter, which may be from about 4 mm to about 11 mm depending on the desired clinical application, can be larger than the outer diameter of the prosthesis by a factor of 15% to 25% to attain the final diameter post heat treating. In one embodiment, a 10 mm in diameter device would be fabricated/heat treated on a 12 mm OD mandrel.

The biodegradable polymer is preferably interwound radially to an inner membranous layer, and can be annealed together, in some embodiments, at temperatures ranging from 300 to 500 degrees Fahrenheit.

The biodegradable filament layer 201 can also be annealed on a mandrel or otherwise attached to the inner layer 200, as illustrated schematically in FIG. 1. Shown first is a first tubular body 200 then a helically wound and braided polymer body 201. The multi-layered stent may be formed in some embodiments by annealing layers 200 and 201. The first tubular body 200 preferably has a smaller diameter than the second tubular body 201 such that the first tubular body 200 becomes the inner layer and the second tubular body 201 becomes the outer layer. One or more drug release layers 202 may be present on one or more surfaces of layers 200 and/or 201 as previously noted.

The prosthesis is preferably configured to be at least partially bioresorbable and can in some embodiments, degrade in vivo over 1-3 years. Heavy molecular weight polymers possess higher tensile strength and would require additional time to intergrade to the vascular site.

One embodiment of a bioabsorbable polymeric layer 10 is illustrated generally in FIGS. 3 and 4. Biodegradable stent layer 10 is generally tubular and formed from two sets of oppositely-directed, parallel, spaced-apart and helically wound elongated strands or filaments 12. The sets of filaments 12 are interwoven in an over and under braided configuration intersecting at points such as 14 to form an open mesh or weave construction. As described in greater detail below, at least one and preferably all filaments 12 are made of one or more commercially available grades of polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester; poly(amino acids), poly(alpha-hydroxy acid) or related copolymers materials. Methods for fabricating stents 10 are generally known and disclosed, for example, in U.S. Pat. No. 4,655,771 to Wallsten and U.S. Pat. No. 5,061,275 to Wallsten et al., hereby incorporated by reference in their entirety.

Stent layer 10 is shown in its expanded or relaxed state in FIGS. 3 and 4, i.e., in the configuration it assumes when subject to no external loads or stresses. The filaments 12 are resilient, permitting the radial compression of stent layer 10 into a reduced-radius, extended-length configuration or state suitable for delivery to the desired placement or treatment site through a body vessel (i.e., transluminally). Stent layer 10 is also self-expandable from the compressed state, and axially flexible.

Stated another way, stent layer 10 is a radially and axially flexible tubular body having a predetermined diameter that is variable under axial movement of the ends of the body relative to each other. The stent layer 10 is composed of a plurality of individually rigid but flexible and elastic thread elements or filaments 12, each of which extends in a helix configuration along a longitudinal center line of the body as a common axis. The filaments 12 define a radially self-expanding body. The body may be provided by a first number of filaments 12 having a common direction of winding but axially displaced relative to each other, and crossing a second number of filaments 12 also axially displaced relative to each other but having an opposite direction of winding.

The tubular and self-expandable body or structure formed by the interwoven filaments 12 is a primary prosthetically-functional structure of stent layer 10. However, it is known that other structures and features can be included in stents, and in particular features which enhance or cooperate with the tubular and self-expandable structure or which facilitate the implantation of the structure. One example is the inclusion of radiopaque markers on the structure which are used to visualize the position of the stent through fluoroscopy during implantation. Another example is the inclusion of a covering 15 or additional interwoven filaments, for instance, to reduce the porosity or open spaces in the structure so that the stent can be used to prevent tissue in-growth or be used as a graft. Other examples include collapsing threads or other structures to facilitate repositioning and removal of the stent. Furthermore, many of the desirable features and properties of stent layer 10 will be present if some, but not all, of the filaments 12 are made of a bioabsorbable polymeric material.

An implantable bioabsorbable stent layer 10 may be made by a preferred method of braiding such that 10-36 independent strands, such as 24, 30, or 36 strands for example, of 0.15-0.60 mm diameter bioabsorbable polymeric filament are interwoven into helical shape strands on a round bar mandrel of 3-30 mm diameter such that one-half of the number of helical strands are wound clockwise and one-half are wound counterclockwise and such that each clockwise helical strand is adjacent (interbraided) to a counterclockwise strand, the tubular braid is made with strand braid angles (angle between two filaments in the longitudinal or axial direction) of 120-150 degrees (pitch angles, i.e., the angle between a filament and transverse axis of the stent that may be between about 15-45 degrees) while on the braid bar mandrel, the braid is slid off of the braid bar and onto a 0.2-10 mm smaller diameter annealing bar or tube mandrel, each end of the braid pulled or compressed to cause axial extension or compression of the braid on the anneal mandrel, or left free, and each end of the braid secured on each end of the anneal mandrel to fix the preset axial position of the braid, or left free, annealing the braid on the anneal mandrel at a temperature between the glass-transition temperature and melting temperature of the polymer for 5-120 minutes in air, vacuum, or inert atmosphere, cooling the annealed braid on the anneal mandrel to about room temperature, sliding the braid off of the anneal mandrel and cutting it to the desired stent length. Another preferred embodiment includes at least one bioabsorbable-radiopaque marker strand.

Sterilization

The prostheses and delivery system components as described herein can be sterilized by a variety of processes, including ethylene oxide (EtO) with a relatively short degassing cycle, radiation (gamma or e-beam) or heat (steam or dry) processes. Other relatively low temperature processes that can be used include vaporized hydrogen peroxide, hydrogen peroxide gas plasma, or ozone.

A relatively new sterilization process relies on oxides of nitrogen, and principally, nitrogen dioxide. Such a process can be useful, for example, for a combination device that includes a drug delivery characteristic. In the presence of oxygen (air), nitric oxide reacts to form reactive nitrogen species (RNS) including nitrogen dioxide (NO2) and, to a much lesser concentration, its dimer, dinitrogen tetroxide (N2O4). Other transient species may be present at low concentrations (<1 ppm), including: nitrogen trioxide (NO3), dinitrogen trioxide (N2O3), dinitrogen pentoxide (N2O5), and nitrous oxide (N2O). In a sterilization chamber where NO is mixed with air, most of the NO reacts to form NO2. The only other oxide of nitrogen that forms under these circumstances and is stable at concentrations higher than 1 ppm is N2O4, which exists in equilibrium with NO2 and the concentration of which is determined by the NO2 vapor pressure. If the air is humidified, NO2 can be converted into nitric acid (HONO2) at trace levels.

A recently developed sterilization process uses low concentrations (less than about 30, 25, 21, 20, 15, or less mg/L) of nitrogen dioxide gas in the presence of air and water vapor. The process is typically delivered at or near room temperature and consists of evacuation of air from the chamber, the introduction of the sterilant, and the addition of humidified air to a preset pressure, which is typically at or near ambient pressure. Depending on the physical design and packaging of the device to be sterilized, the sequence of: vacuum sterilant injection humid air injection may be repeated several times or the sequence can be changed. At the nitrogen dioxide concentrations used, and considering the operating temperature and pressure of the process, the NO2 remains in the gas phase and acts as an ideal gas throughout the sterilization cycle.

It has been determined that in the gas sterilization process NO2 is the key sterilizing agent. Other RNS may contribute in less-significant ways. Although the literature cites many other potential reactions, the specific environment established with the sterilization system limits the chemical species formed and the breadth of biological response. This limit allows the process to be focused and controlled.

Gas reactions that occur in the sterilization chamber are predictable and have been determined by calculation, computer modeling, and empirically. The sterilant gas concentration mixtures over time are predictable. The reaction rates and resulting concentrations of NO2 and other oxides of nitrogen that result from the reaction of air and NO have been calculated. The starting concentration was set at 0.1% NO in air. NO reacts with oxygen in the air to create NO2. The constant sum of NO and NO2 indicates that these two molecules account for almost all of the nitrogen present. The calculations predict a rapid conversion of NO to NO2 with only trace amounts of N2O4 due to the low NO2 concentration. NO2 is an effective sterilant at low concentrations, often between 6 and 12 mg/L, 8 and 10 mg/L and typically less than 21 mg/L, depending on the application. Therefore, relatively small containers of the NO2 are required.

FIG. 5 is a cross-sectional view of one of the polymeric filaments 12. As shown, the filaments 12 may be substantially circular in cross section, although other configurations such as oval or rectangular (ribbon) may be used.

In some embodiments, the polymeric filament intermediate layer described above can be operably attached, such as radially interwound to a biocompatible inner tubular membrane layer. The membrane is preferably a synthetic material such as, for example, a thermoplastic such as ePTFE, Teflon, polyethylene, or polyurethane. In some embodiments, the membrane and the polymeric filaments may be annealed together, such as, for example, at a temperature ranging from about 300° F. to about 500° F. This layer can be the inner lumen layer, although it could also be an outer layer, or both an inner and outer layer to promote cellular in-growth.

In some embodiments, a lumen layer, such as an inner or outer layer includes a porous media feature network of open-celled directional pores for enhanced fluid dynamics. In some embodiments, the pore size may be constant throughout the membranous layer. The prosthesis may also be prepared with different mean pore sizes. Pore size can be an important parameter in that certain macromolecular drugs may be excluded from use where the pore size is very small. The pore size may also play a role in determining the extent of cellular infiltration or tissue in-growth during implantation of the stent. While cellular in-growth is sometimes desirable, it can also lead to complications such as infection and difficulty in removing the stent. Stents with a mean pore size of greater than about 10 microns can allow infiltration of cellular sized biomaterials; stents with mean pore sizes in the range of 1-10 microns may accommodate infiltration of some of the above bio-materials. Stents with pore sizes less than about 1 micron will not generally accommodate infiltration of any of the above biomaterials but can accommodate infiltration of macromolecular and small biomaterials. Thus, the pore size of the stent may be varied to foster or inhibit cellular infiltration and/or tissue in-growth. Of course, the pore size may also be varied to facilitate delivery of drugs of different molecular sizes. Furthermore, the pore size and overall porosity of the membrane layer can be predetermined for a particular clinical application in order to control the mass loss as well as drug elution, and thus the degradation rate of the stent, caused, for example, by high velocity blood flow through the stent. In some embodiments, the porous membrane layer can be configured such that the stent maintains at least about 50% of its radial strength for a period of at least 3 months, 6 months, 9 months, 12 months, 18 months, 2 years, 3 years, 4 years, 5 years, 7 years, 10 years, or more.

Optionally present in one or more of the layers are radiopaque marker elements to improve visualization of the stent, for example, under fluoroscopy. Also the delivery system/catheter may possess radiopaque markers defining the distal and proximal end of the vascular prosthesis while in the delivery system. The flexible nature and reduced radius of the compressed prosthesis enables it to be delivered through relatively small and curved vessels in percutaneous transluminal angioplasty. In some embodiments, the marker elements can either be located directly adjacent the ends of the stent in a manner only slightly increasing a length of the stent or the marker elements can be spaced from the adjacent portions of the stent in a manner causing the marker elements to enhance somewhat the overall length of the stent. With the radiopaque marker elements in place attached to the ends of the stent, the location and orientation of the stent can be precisely determined both before, during, and after implantation and radial expansion of the stent within the body lumen. In some embodiments, the radioopaque marker elements are made of a metal or a metal alloy, such as, for example, one or more of nitinol, Elgiloy®, Phynox®, MP35N, stainless steel, nickel, titanium, gold, rhenium, tungsten, palladium, rhodium, tantalum, silver, ruthenium, and hafnium. The marker element could be a 90% platinum and 10% iridium alloy in one particular embodiment.

FIG. 6 illustrates a schematic cut-away view of a portion of the wall of a stent 100 that may be as in FIG. 1 with an inner layer comprising a plurality of bioabsorbable polymer filaments 14. In some embodiments, the filaments 14 are radially interwound with ePTFE, nylon, polypropylene, or another biocompatible material. The stent 100 also comprises an outer layer 102 with a controlled-mass release and/or drug release element, such as, for example, polyphosphoester microspheres. The outer layer 102 may be, in some embodiments, spray-dipped, coated, annealed, bound covalently or noncovalently to the inner layer. Thus, the outer layer may be a tubular layer as illustrated in FIGS. 1 and 2c or it may be a layer of coating surrounding a portion or all of the individual fibers in the intermediate woven layer as shown in FIG. 6.

FIG. 7 illustrates schematically a cross-section through a stent, according to one embodiment of the invention. The cross-sectional shape 204 of the stent may be non-circular, and may be acorn-shaped as shown. While the device is inserted/loaded in the delivery system, the constructed embodiment tends to take a set shape, this condition directly relates to the delivery system OD size, and the stent folding methods in the delivery system/catheter as described below. Once the sheath of the delivery system/catheter is pulled back in a proximal direction and the device is released at the target site the device then transforms into a round and circular shape through flow through the inner lumen. Initially it may create a better lodging condition once the device has intergraded in the vascular site it would contour to the specific shape of the body lumen.

FIGS. 8-11 illustrates several non-limiting examples of the self-expandable stent in a compressed configuration. The compressed shape may be, for example, U-shaped 400 as shown in FIG. 8, W-shaped 402 as shown in FIG. 9, "carpet rolled" 404 as shown in FIG. 10, or "starburst" radially compressed shape 406 as shown in FIG. 11. One of ordinary skill in the art will appreciate that many other compressed prosthesis configurations are possible that do not necessarily have to be compressed radially inwardly.

The prosthesis of the present invention can be implanted in various locations. In addition to the large coronary vessels such as the left main, circumflex, left anterior descending, or right coronary artery, the stent may advantageously be placed in the smaller branches of the coronary arteries, such as the diagonals, marginals or posterior descending artery, or various peripheral vessels such as the ascending or descending aorta, internal mammary, brachial, femoral, carotid, or Circle of Willis cerebral vessels. The stent is also particularly advantageous for curved and tortuous vessels, some of which are mentioned above. The specific features includes but not limited to self expanding design, diameters and length specifications, and drug delivery reservoirs. The prosthesis may also be placed in veins such as the internal or external jugular vein, superior or inferior vena cava, femoral vein, or great saphenous vein, and non-vascular lumens such as the biliary tree, esophagus, intestines, ureters, urethra, trachea, bronchi, fallopian tubes and the like.

In some embodiments, a peripheral (non-coronary) stent may have a length of between 5-20 cm, a wall thickness of 0.009 of an inch to 0.015 of an inch, a compressed outside diameter of 7 French to 15 French and an unfolded outside diameter of 4 cm to 11 cm. For coronary applications, the end device may possess the following parameters in certain embodiments: 2-5 mm outer diameter; 10-40 mm length; 0.004-0.007 inch wall thickness.

FIG. 11A illustrates an embodiment of a stent 1000 that can be as described previously, with a proximal end 500, distal end 502, and additionally one, two, or more side orifices 504 disposed within the sidewall of the stent 1000. In some embodiments, a stent 1000 can have at least 2, 3, 4, 5, 6, 7, 8, 9, 10, or more side orifices 504. The side orifices 504 can be advantageously dimensioned to, for example, promote blood flow to side-branch arteries that may otherwise be blocked or limited by a stent placed across a main vessel. Some non-limiting examples of side-branch vessels can include, for example, the acute marginal, posterior descending artery, obtuse marginal, septal perforators, and diagonal arteries of the coronary arterial circulation.

If a plurality of side orifices 504 are present, they can each be aligned in a number of ways depending on a particular patient's vascular anatomy and the desired clinical result. In some embodiments, the side orifices 504 can be arranged along an axis parallel to the longitudinal axis of the stent 1000 as shown in FIG. 11A or longitudinally offset from each other as shown in FIG. 11B. FIG. 11C illustrates a stent 1000 as described and illustrated above and disposed within a lumen of a main vessel 516. As illustrates a first side orifice 504 is sized to promote blood flow to a first side branch vessel 518, and a second side orifice 504' is sized to promote blood flow to a second side branch vessel 520. In some embodiments, the side orifices 504 in total can make up at between about 1% and 80% of the total surface area of the outside diameter of the stent, such as between about 5% and 60%, or between about 31% to 61% in some embodiments. In some embodiments, a side branch orifice 504 may have a diameter of between about 1 mm and about 5 mm. In some embodiments, one or more therapeutic agents as described elsewhere herein can be concentrated around side orifices 504 to better prevent thrombosis or stenosis across the side orifices 504.

Figure 11E:
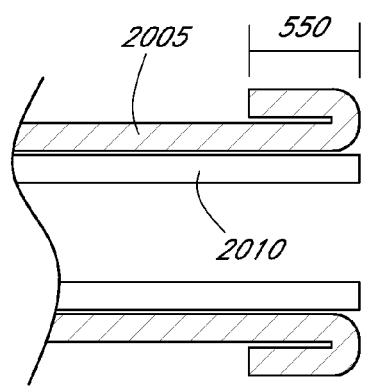
Figure 11F:
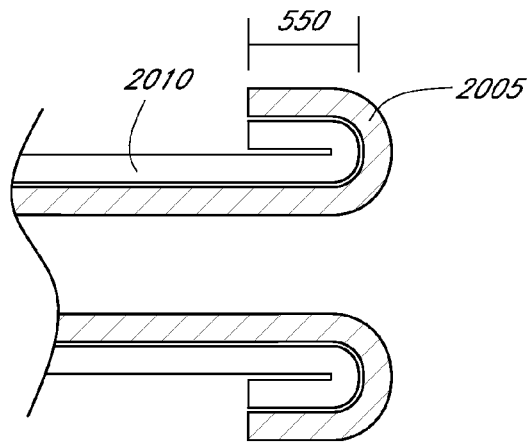

In some embodiments, a stent can include one or more radially enlarged ends similar to that described in connection with FIG. 2A above, that can be formed by folding one or more layers of the stent back over one or both of the proximal end and/or the distal end of the stent. The enlarged, folded ends can then be secured by a variety of methods, such as, for example, suturing, adhesives, annealing, or the like as will be described in greater detail below. The stent can include one, two, three, or more layers as previously described. As illustrated in FIG. 11D, in one embodiment, a stent 1000 has a proximal end 500 and a distal end 502 and includes a braided layer 2010 and a porous membrane layer 2005 that can be as previously described. An optional drug delivery characteristic described elsewhere in the application is not shown for clarity. As illustrated, one or more segments 550 of the porous membrane layer 2005 at the proximal end 500 of the stent 1000 is folded over the braided layer 2010. In some embodiments, the folded segment 550 can have a length from about 0.01 inches to about 0.10 inches, such as from about 0.30 inches to about 0.50 inches, or about 0.40 inches in other embodiments. FIG. 11E illustrates another embodiment of a folded stent end with the porous membrane layer 2005 being the outer layer relative to the braided layer 2010 and having a portion 550 folded over itself. FIG. 11F illustrates yet another embodiment where a segment 550 of both the membrane layer 2005 and the braided layer 2010 are folded over themselves.

Figure 11G:
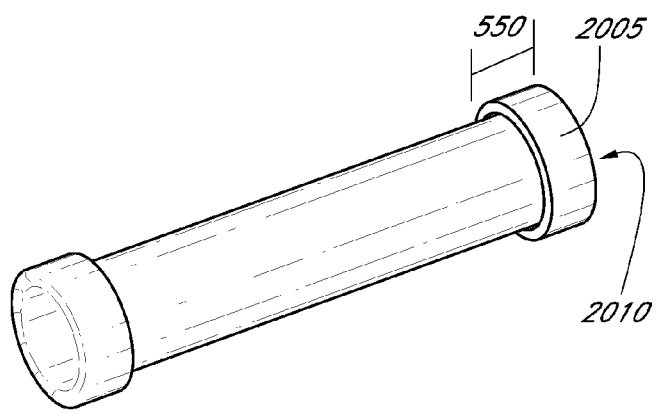
FIG. 11G illustrates a perspective view of a stent with folded end segments, in accordance with one embodiment of the invention.

FIG. 11G illustrates a perspective view of a stent 1000 with radially enlarged proximal 500 and distal 502 ends resulting from folding over of one, two, or more layers as previously described.

Figure 11H:
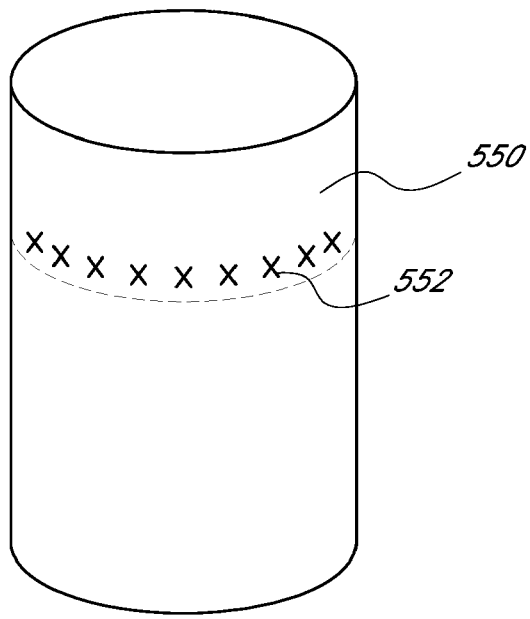
FIGS. 11H-11I illustrate schematic views of various suturing patterns over folded portions of the stent in order to secure multiple stent layers together, in accordance with some embodiments of the invention.
Figure 11I:
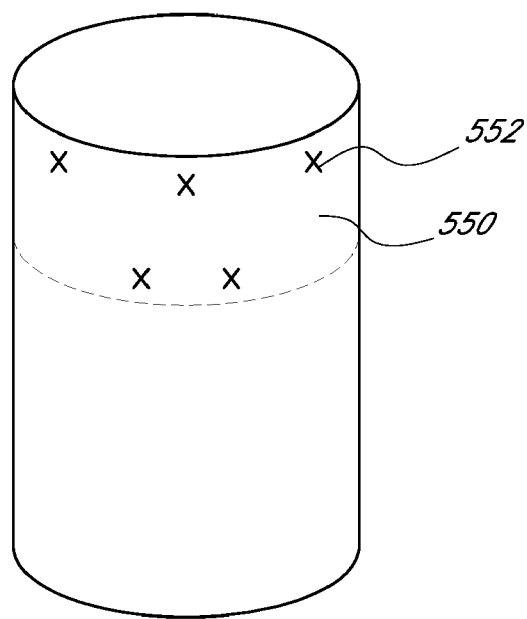

FIG. 11H schematically illustrates an end of a stent with a folded portion 550 as previously described. The membrane layer 2005 and the braided layer 2010 can be attached mechanically by suturing the two layers 2005, 2010 together using any appropriate suture material, such as, for example, a suture made of a biodegradable material disclosed elsewhere in the application, catgut, PTFE, ePTFE, polyester, polyglycolic acid, poliglecaprone, nylon, polyethylene, polypropylene, or polyurethane, depending on the desired clinical result. The sutures could be, for example, simple interrupted sutures or continuous running sutures. As illustrated in FIG. 11H, tied suture loops 552 are illustrated attaching the membrane layer 2005 and the braided layer 2010 together over the folded portion 550 of the stent. The sutures 552 can be tied in a plane generally perpendicular to the longitudinal axis of the stent as illustrated in FIG. 11H, in a zig-zag pattern in another embodiment as illustrated in FIG. 11I, or in other patterns as known in the art. In other embodiments, the sutures 552 are also attached in an area of the stent where there is no folded over portion (e.g., toward the midpoint of the stent). Any number of suture loops can be utilized, such as 1, 2, 3, 4, 5, 6, 7, 8, 9, 10, or more. The sutures 552 could be attached to the stent near the proximal end, distal end, or both. In other embodiments, other attachment techniques such as an adhesive, e.g., fibrin glue can be used to attach two or more stent layers together. In some embodiments, one or more ends of the stent could be heat-treated as described above to enhance attachment of the layers together, for example. By overlapping the thin layer of synthetic membrane over the braided structure, it is possible to conceal and secure the radiopaque markers, such as between two layers of a fold, and avoid undesirable marker detachment and migration into the bloodstream. The overlapping of the thin layer of membrane could also provide a better radial support and better fluid dynamics at one or both ends of the device.

Figure 11J:
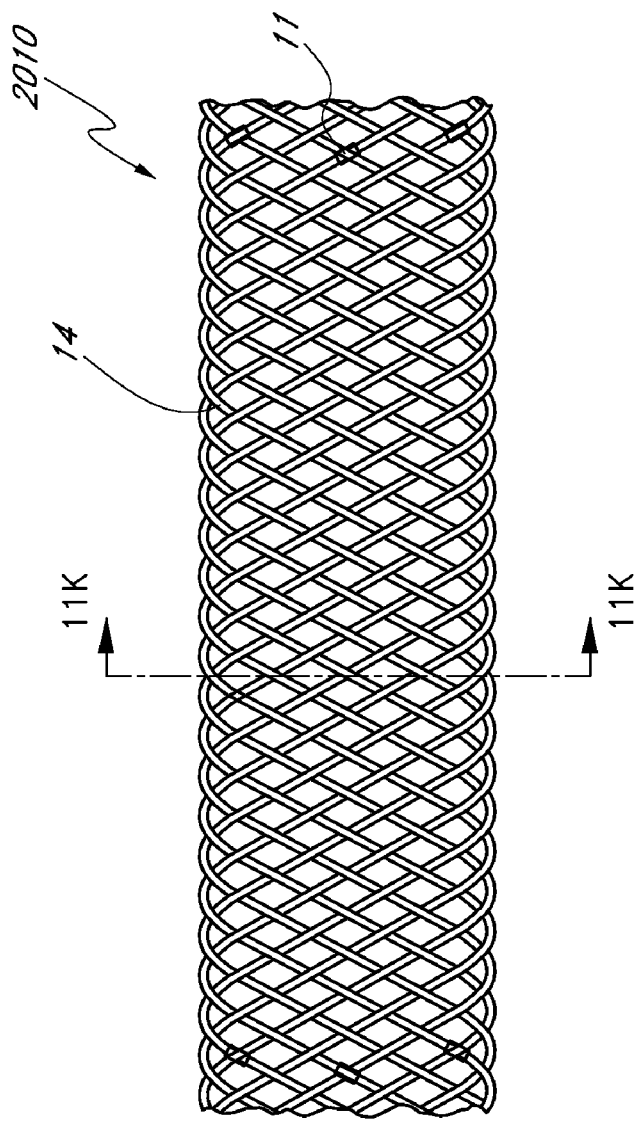
FIG. 11J is a schematic view of a stent having a biodegradable woven layer, according to one embodiment of the invention.
Figure 11K:
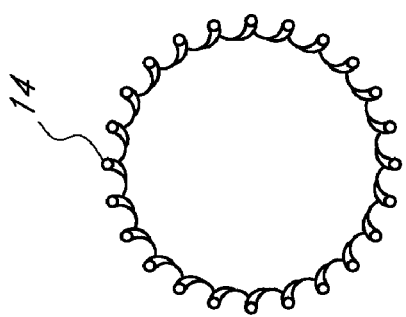
FIG. 11K is a cross-sectional view of the stent of FIG. 11J through line 11K-11K.

FIG. 11J illustrates a perspective view of a stent having a layer of interwound biodegradable filaments 2010, according to one embodiment of the invention. The stent can include one, two or more radioopaque marker elements 11, such as near the proximal or distal ends of the stent as illustrated. FIG. 11K is a cross-section of the stent of FIG. 11J through line 11K-11K of FIG. 11J. The stent could also have additional layers as described elsewhere in the application, including the following embodiments.

Figure 11L:
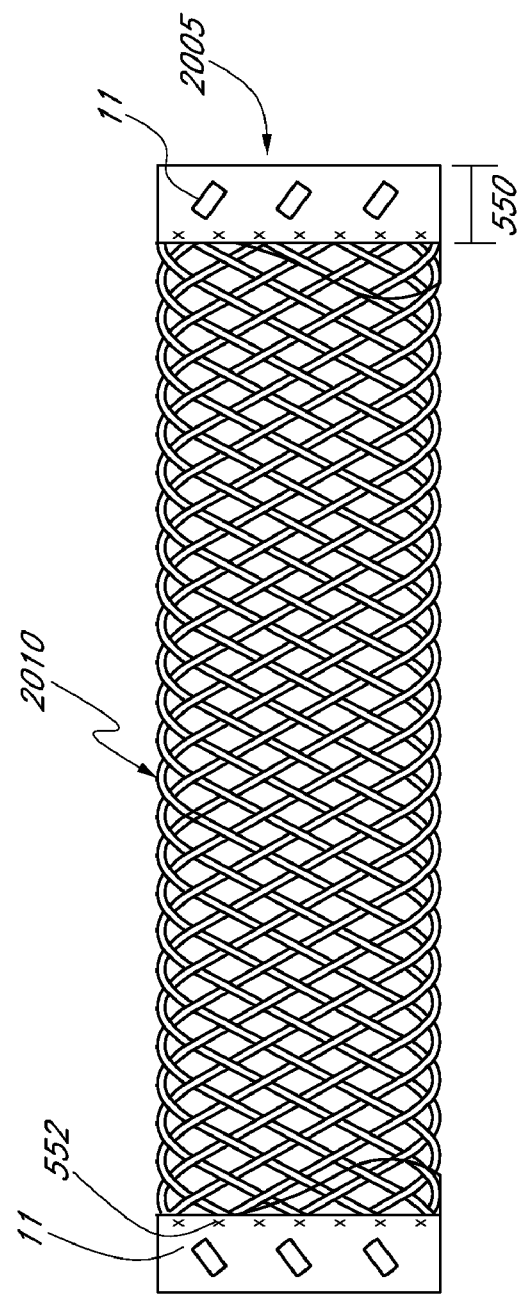
FIG. 11L is a schematic view of a stent having an outer biodegradable woven layer and an inner porous membrane layer, according to one embodiment of the invention.

FIG. 11L illustrates a perspective view of a stent having an outer braided layer 2010 and an inner membrane layer 2005 with a folded portion 550 of the inner membrane layer 2005 over the braided layer 2010 as previously described. As illustrated, the layers 2005, 2010 are attached together using sutures 552, such as near both the proximal 500 and distal 502 ends as shown. The stent can also include one or more radioopaque marker elements 11, such as at least 1, 2, 3, 4, or more marker elements 11 disposed near either the proximal end 500 and/or the distal end 502 of the stent, although other alternative or additional locations, such as near or at the midpoint of the stent are also within the scope of the invention. In some embodiments as shown, the radioopaque marker element is mechanically secured in between the braided layer 2010 and the folded portion 550 of the membrane layer 2005. However, the marker could also be placed in between the braided layer 2010 and membrane layer 2005 in embodiments where no folded portion 550 is present. The radioopaque markers 550 can bioincorporate in the luminal wall and remain visible under fluoroscopy following biodegradation of the stent. The marker element 11 could be either solid or hollow, and any appropriate shape, such as circular, cylindrical, triangular, or rectangular. In some embodiments, the marker element is cylindrical and hollow with a length of between about 0.01 inches to about 0.1 inches, such as about 0.035 inches. In some embodiments, the marker element 11 could have an inner diameter of between about 0.005 inches to about 0.020 inches, such as between about 0.0095 inches and about 0.0145 inches. In some embodiments, the marker element 11 could have a wall thickness of between about 0.001 inches to about 0.005 inches, such as between about 0.0015 inches and about 0.0025 inches.

In some embodiments for coronary applications, the stent could have an outer diameter of from about 1 mm to 4.5 mm in some embodiments. In peripheral applications, the stent could have an outer diameter of from about 5 mm to 15 mm, or about 7 mm in some embodiments. The stent could have a constrained outer diameter during delivery of from about 1.5 mm to about 5.5 mm, such as about 3.5 mm in some embodiments. The stent could have a length of the overlapped folded portion to be between about 0.030 to 0.060 inches, or between about 0.030 and 0.040 inches in some embodiments, and a total length of about 2-20 cm, or about 10 cm in some embodiments.

FIG. 11M illustrates a perspective view of a stent similar to FIG. 11L, except that the membrane layer 2005 is the outer layer with respect to the braided layer 2010. At least one of the layers, such as the membrane layer 2005 can have a folded-over portion 550 to secure the marker elements 11 and have suture loops 552 or other attachment means as previously described. A cross-section through lines 11N-11N of the stent is illustrated in FIG. 11N.

Figure 11O:
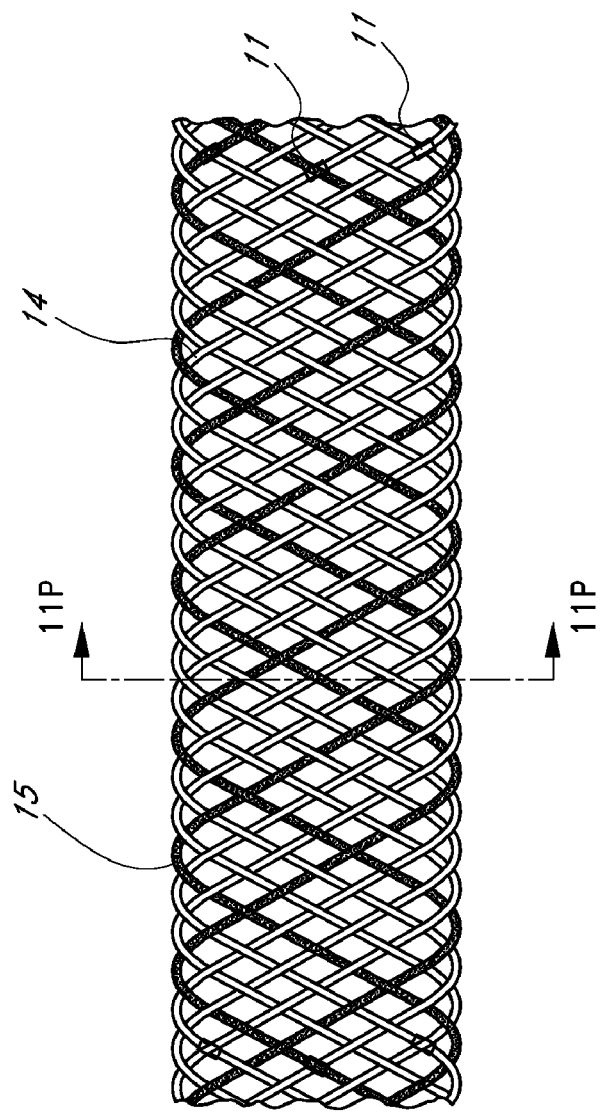
FIG. 11O is a schematic view of a stent having a hybrid weave of biodegradable fibers and metallic fibers, according to one embodiment of the invention.
Figure 11P:
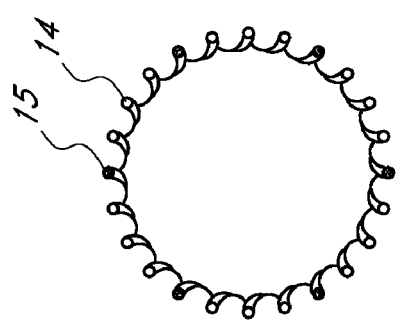
FIG. 11P is a cross-sectional view of the stent of FIG. 11O through line 11P-11P.

FIG. 11O illustrates a perspective view of a braided layer 2010 of a hybrid stent made up of interwoven strands of both bioabsorbable fibers 14 as previously described as well as nonbioabsorbable fibers, such as metallic strands 15. The metallic strands 15 can include materials, such as, for example, nitinol, Elgiloy®, Phynox®, MP35N, stainless steel, or another metal or alloy. In one embodiment, the stent includes 24 stands, 18 made of a bioabsorbable material such as PLA, and 6 strands made of a metallic material. However, any number of bioabsorbable and nonbioabsorbable could be used for stent construction, as previously described, such as, for example, 36 strands, of which 27 are bioabsorbable and 9 metallic. In other embodiments, between about 4% and 96%, such as between about 16% and 84%, 16% and 50%, or about 25% of the strands are made of a metallic material. In some embodiments, less than about 70%, 60%, 50%, 40%, 30%, 20%, 10%, or less of the strands are made of a metallic material. The metallic strands 15 could be interspersed with the bioabsorbable fibers 14 at regular intervals throughout the braid, such as every other, $3^{rd}$, $4^{th}$, $5^{th}$, $6^{th}$, $7^{th}$, $8^{th}$, $9^{th}$, or more strand being a metallic strand 15, or interspersed irregularly depending on the desired clinical result. The stent could also optionally include have an inner and/or outer membrane layer 2005 (not shown), and also a drug delivery characteristic as previously described. A cross-section through lines 11P-11P of the stent is illustrated in FIG. 11O. A hybrid bioabsorbable-metallic stent could advantageously result in a reduced loss of radial strength over a period of time. Late recoil (negative remodeling) is one of the most important causes of restenosis following bioabsorbable stent implantation. As the vessel heals, the artery tends to shrink. Due to their intrinsic high radial force, metallic stents maintain the scaffolding effect over time, thus preventing this phenomenon. To the contrary, pure bioabsorbable scaffoldings lose radial strength relatively quickly allowing the artery to recoil more rapidly. By combining a metallic scaffolding with a bioabsorbable material one could advantageously maintain an appropriate radial force over time allowing the absorption process to take place, avoiding negative remodeling. In some embodiments, the residual metallic component could be a small fraction of what is seen today with balloon expandable metallic stents. This design could advantageously obviate the need for radiopaque markers as the metallic component is visible under fluoroscopy.

Delivery Systems

FIGS. 12-19 illustrate various delivery devices and methods that may be used with the prosthesis shown.

Figure 12:
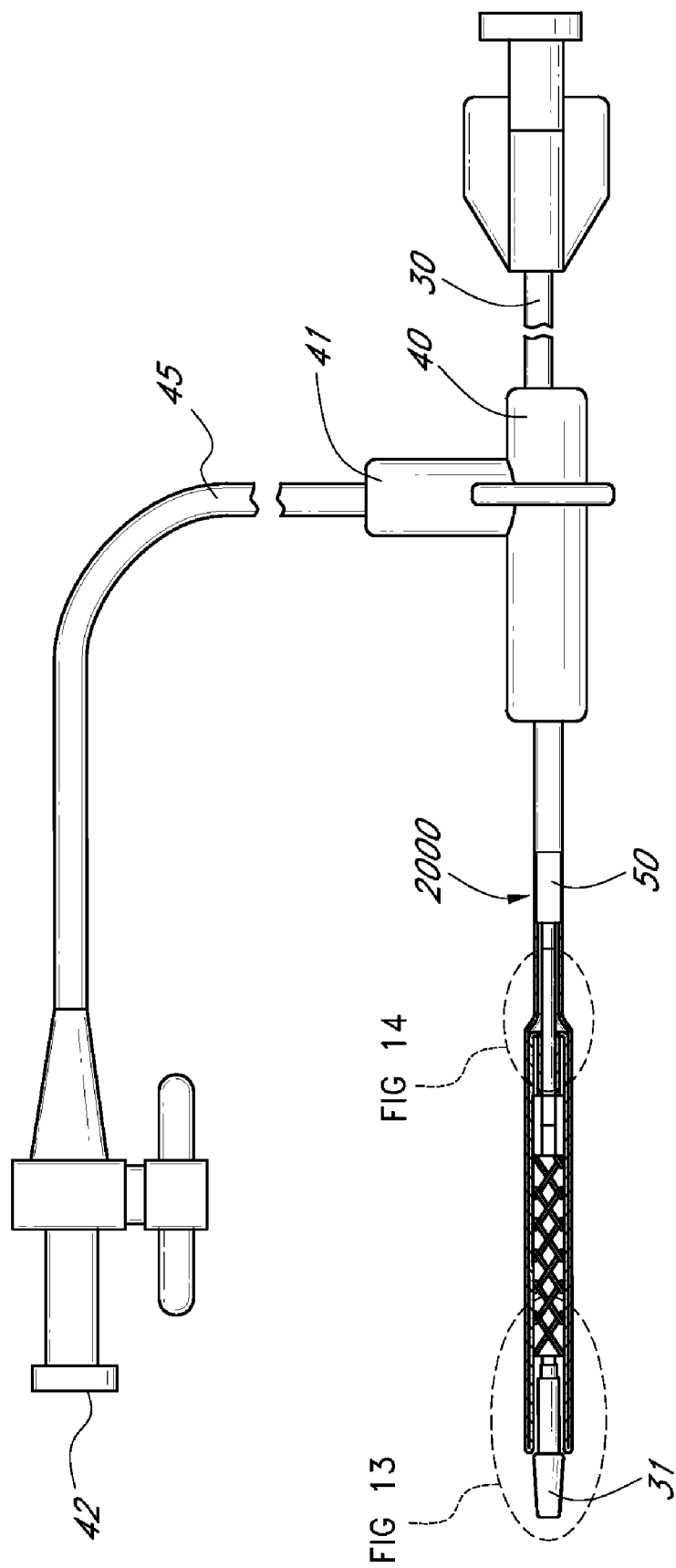
Figure 13:
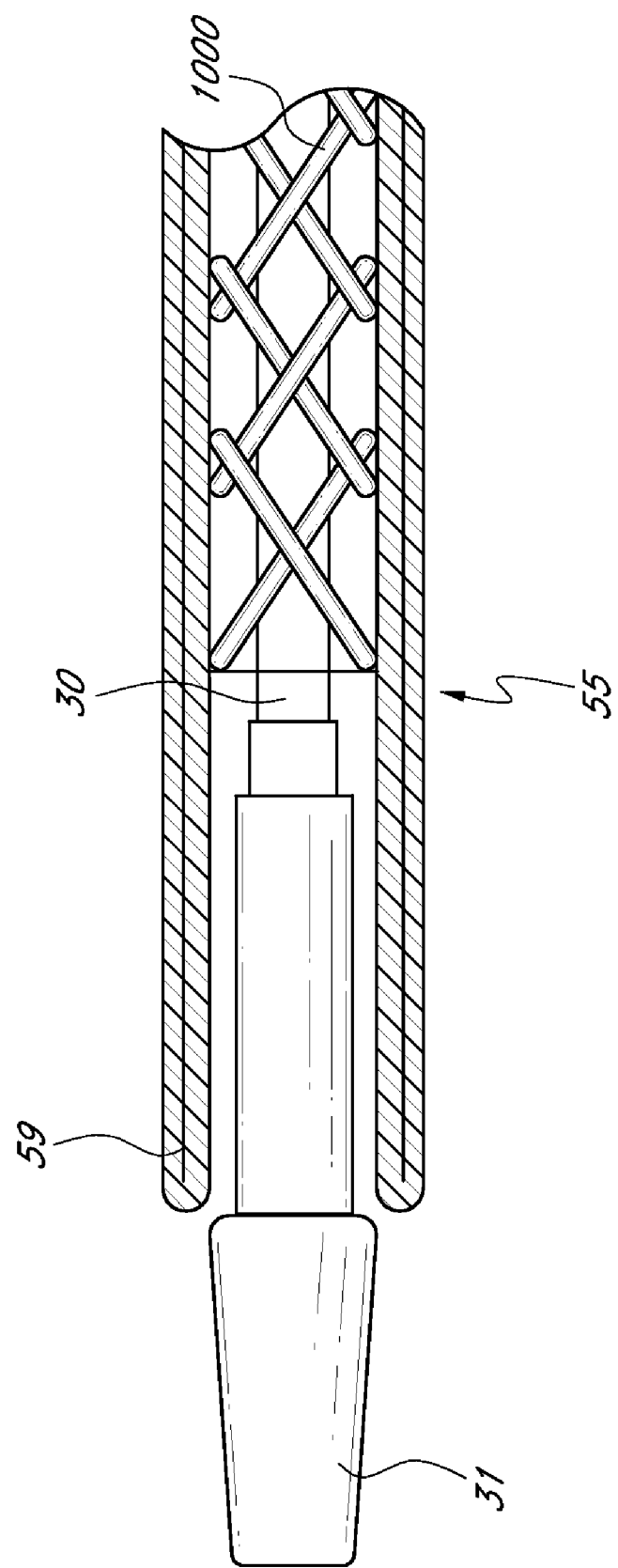
Figure 14:
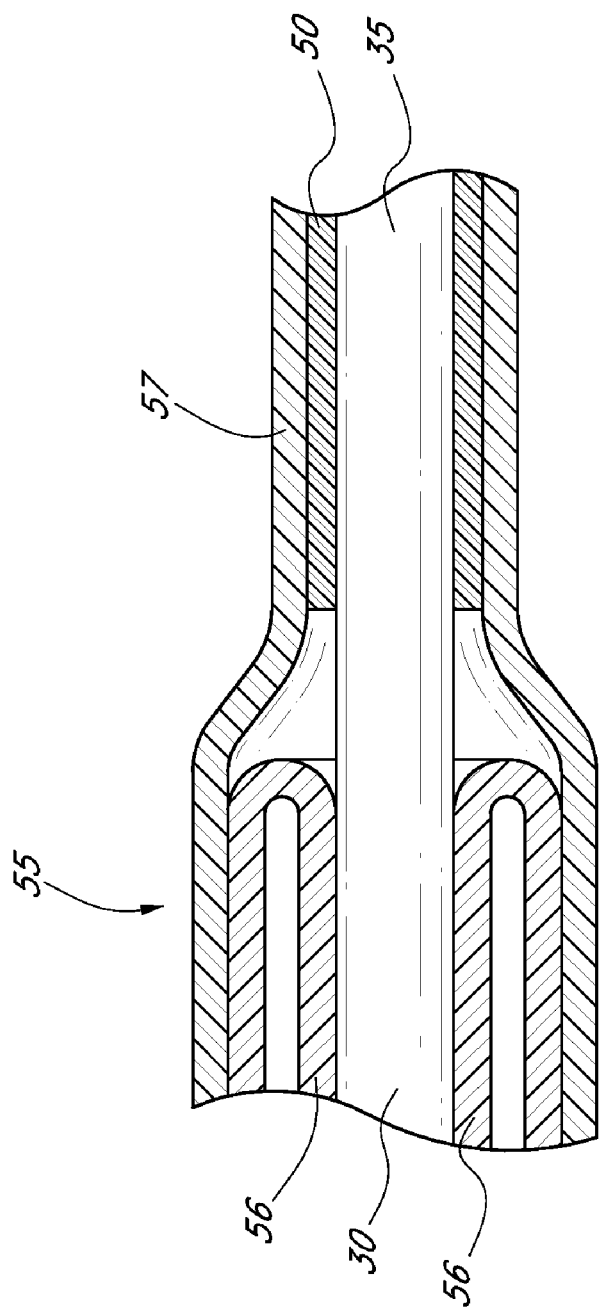
Figure 15:
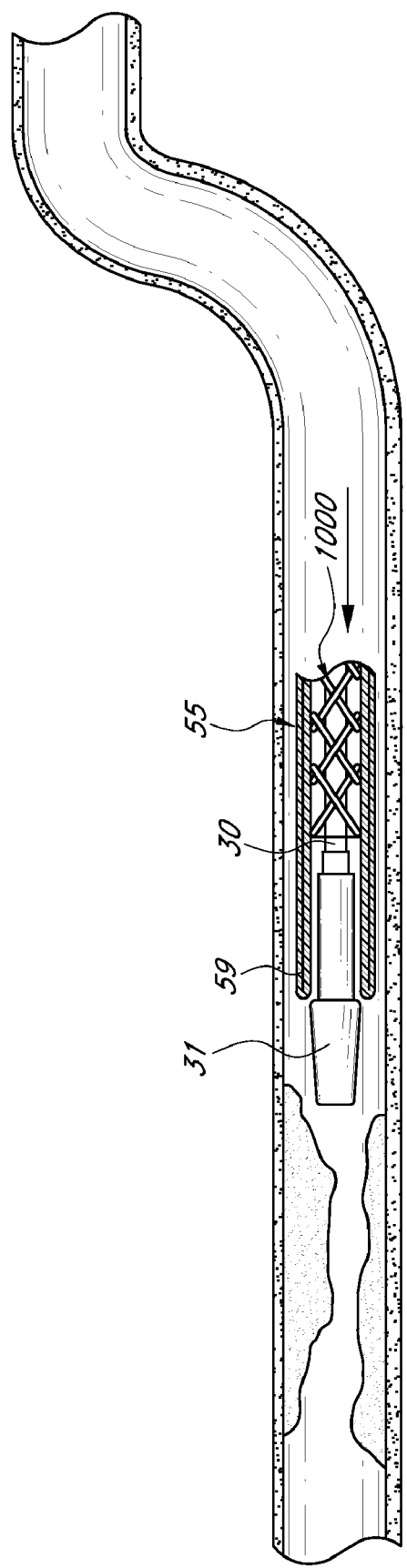
Figure 16:
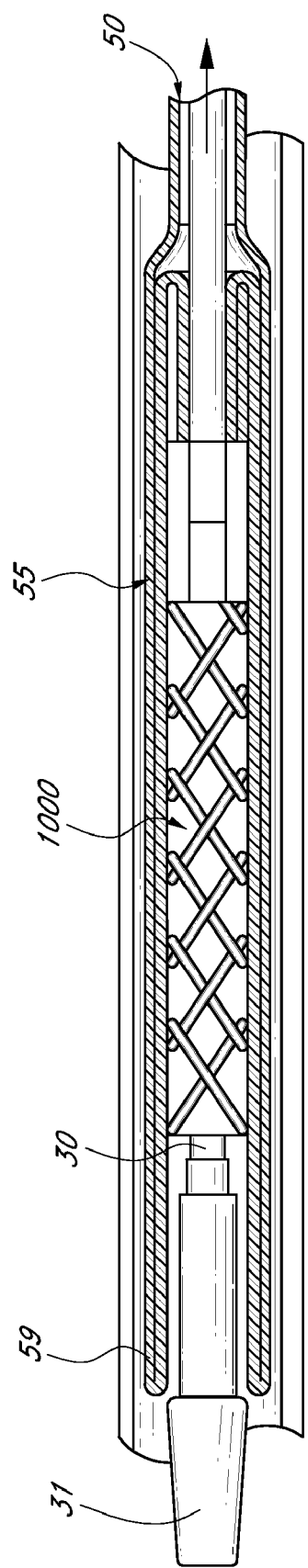
Figure 17:
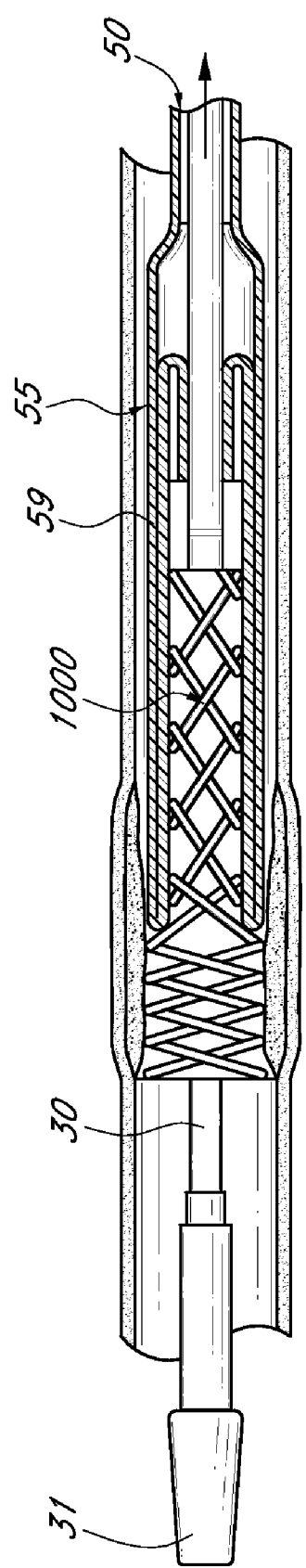
Figure 18:
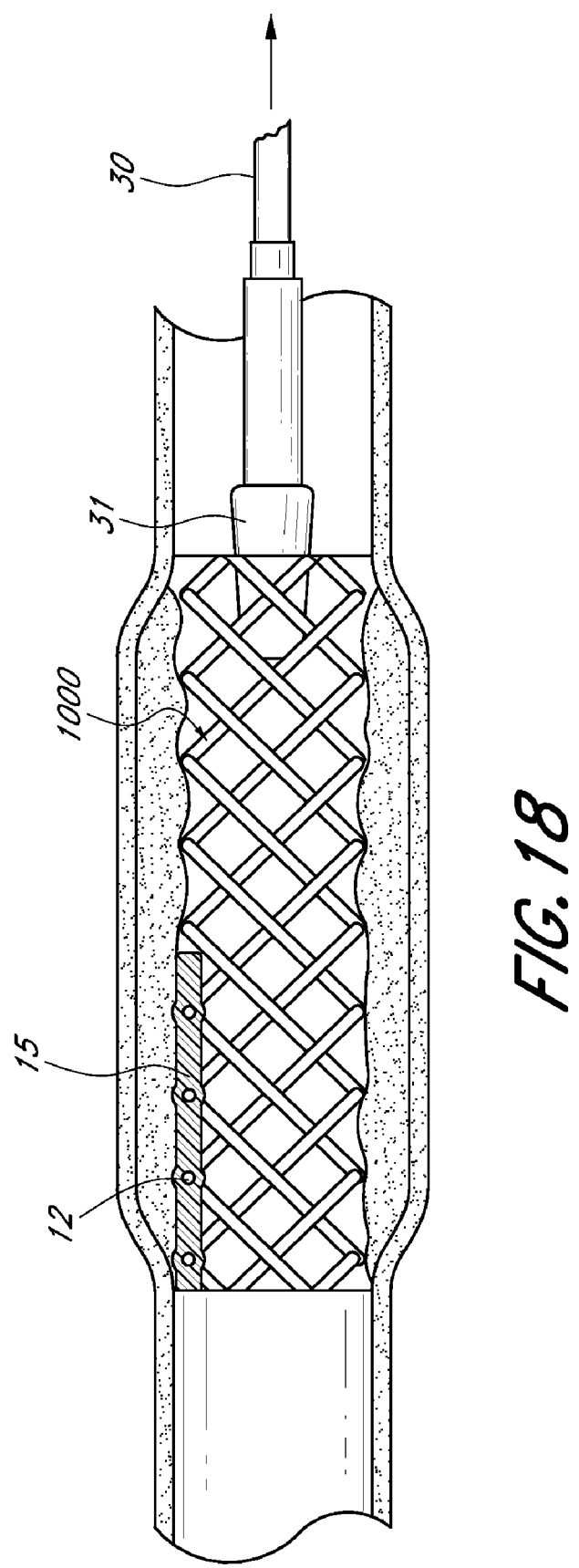

FIGS. 12-14 are illustrations of a coaxial inner/outer tube catheter delivery device 2000 for delivering a stent 1000 to a treatment site in a body vessel. An extension 45 extends from side port 41 to an opening 42.

As shown, stent 1000 may be carried by the distal portion of delivery device 20, and is placed on the delivery device in a radially contracted or compressed state, such as, for example, illustrated in FIGS. 8-11. The proximal portion of delivery device 2000 generally remains outside of the body for manipulation by the operator.

The manner by which delivery device 2000 is operated to deliver stent 1000 to a treatment site in a body vessel or lumen including curved sections is illustrated in FIGS. 15-18. As shown, stent 1000 is placed in a radially compressed state in a surrounding relationship to the outer distal end of inner tube 30. A tip 31 is disposed at the distal end of tube 30. Stent 1000 is constrained on inner tube 30 by the double-walled section of coaxially designed delivery system 55. It is important that stent 1000 not be confined too tightly on inner tube 30. Coaxially designed delivery system 55 should apply just enough force to stent 1000 to hold stent 1000 in place. The double-walled section of coaxially designed delivery system 55 can be removed from around stent 1000 by pulling valve body 40 (see FIG. 12) and proximal tube 50 in a proximal direction. The double-walled section "rolls" off stent 1000. No sliding movements take place between stent 1000 and inner wall 56 (FIG. 14) which contacts stent 1000. Opening 59 are located in the double wall section of the opening 55. Along with the movement of the double-walled section in a proximal direction, the distal end of stent 1000 will be exposed in a radial direction to engagement against the wall of the body vessel. As the double-walled section of the outer member of the coaxially designed delivery system 55 continues moving proximally, more of stent 1000 expands in a radial direction until the entire length of stent 1000 is exposed and engages the wall of a body vessel.

Lumen 35 (FIG. 14) is used to enable delivery device 2000 (FIG. 12) to follow a guide wire (not shown) previously inserted percutaneously into the body vessel. The lumen of inner tube 30 can also be used to introduce a contrast fluid to the area around the distal end of delivery device 2000 so the position of delivery device 2000 can be detected (e.g., through the use of fluoroscopy or X-ray techniques).

The stents of the present invention may be delivered by alternative methods or using alternative devices. For instance, the device described in Heyn et al., U.S. Pat. No. 5,201,757 may be utilized, which is incorporated by reference in its entirety herein.

Figure 19:
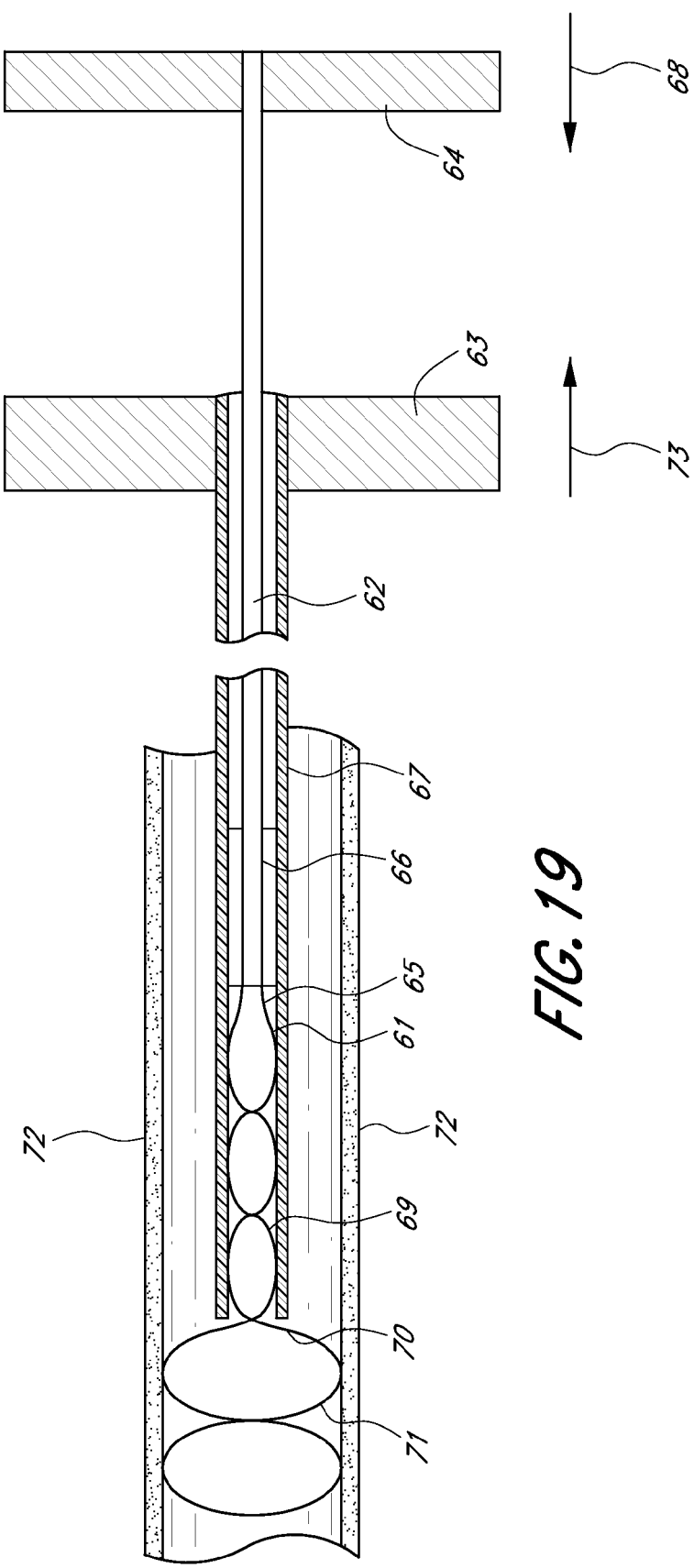

FIG. 19 illustrates a delivery device with an outer tube 61 including member 63 and an inner tube 62 including members 64, 65. Stent 1000 may be inserted in a collapsed state in region 66, and one position of member 65 is shown at about region 67. Member 64 may move in the direction of arrow 68 to push the stent out through end 70 into contact with the interior of wall 72. The stent 1000 is shown as lines 69, 71. The end 70 may be moved by moving member 63 in the direction of arrow 73.

FIG. 20 is a schematic angled perspective view of a stent 402 folded into a "W"-like shape within a delivery catheter 1002. Pusher element 1004 may be used to deploy stent 402 into a desired location in the body lumen, where it can assume its expanded configuration. As described above, the stent 402 with enlarged lateral ends may reduce the risk of undesirable stent migration.

Figure 21A:
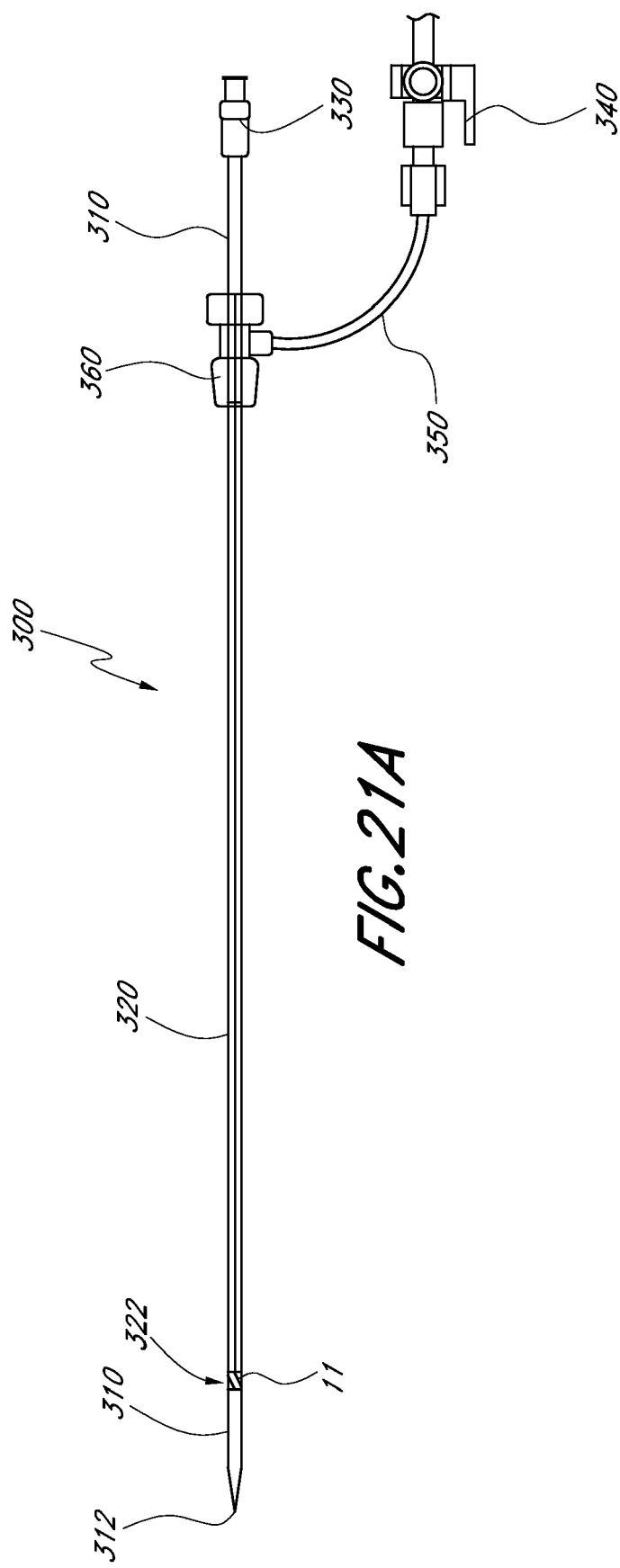

FIG. 21A illustrates a schematic view of an alternative coaxial stent delivery system, according to one embodiment of the invention. The stent delivery system 300 includes an inner tube 310 having a proximal end and a distal end 312, and an outer tube 320 having a proximal end and a distal end 322 configured to slide coaxially over the inner tube 310. A radioopaque marker 11 as previously described can be positioned at or near the distal end 322 of the outer tube 320 as illustrated. In some embodiments, a radioopaque marker 11 can also be placed at or near the distal end 312 of the inner tube 310 as well. In such embodiments with a marker 11 on both the inner tube 310 and the outer tube 320, movement, such as proximal retraction of the inner tube 310 by a distance greater than the length of the stent can serve as an indicator that the stent should expand and be deployed in the desired vessel. Also shown is a proximal Luer port 330 adapted to house a guidewire (not shown) therethrough and/or for infusion or aspiration of fluid, medication, or the like via the inner tube 310 lumen. The proximal end of the outer tube 320 includes a proximal adapter 360 connected via tubing 350 to a check valve 340 for infusion or aspiration of fluid, medication, or the like via the outer tube 320 lumen. In some embodiments, the delivery system can include one, two, or more balloon expansion elements that can each have differing shapes, pressures, and volumes, that can be useful, for example, for "touch-up" procedures. Furthermore, the delivery system can include treating the stent or any other delivery system components with heat or other energy sources for in situ curing and/or molding of the materials.

As described above, a self-expanding stent can be crimped on to inner tube 310 and prevented from expanding during delivery by the presence of the coaxially arranged outer tube 320. The distal end of the delivery system 300 can then deployed to the desired location in the body over a guidewire, for example, a stenosis in a coronary artery. The marker 11 on the distal end 322 of the outer tube 320 can be utilized to facilitate proper positioning. Relative movement of outer tube 320 with respect to inner tube 310, such as in a proximal direction will allow the stent to self-expand.

FIG. 21B is a schematic view of the outer tube 320 with components as previously described. In some embodiments, the outer tube can have an inner diameter from about 0.15 inches to about 0.20 inches, such as about 0.165 inches, and outer diameter from about 0.16 inches to about 0.21 inches, such as about 0.18 inches, a wall thickness of between about 0.005 to 0.002 inches, such as about 0.01 inches, and a length of between about 20 and 40 inches, such as about 27 inches in some embodiments.

Figure 21C:
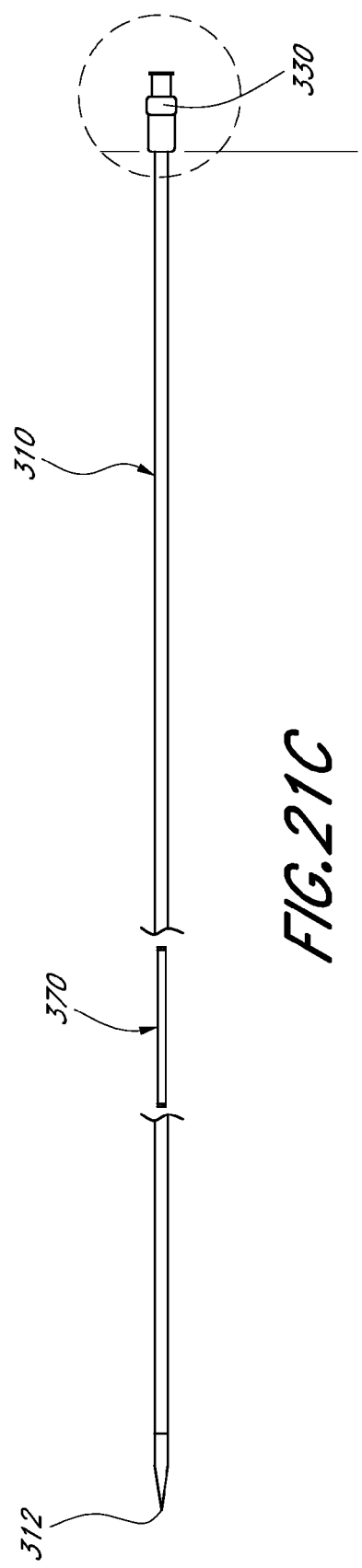

FIG. 21C is a schematic view of the inner tube 310 with components as previously described, also including hypotube 370 within inner tube 310.

Multi-Stent Delivery System

In some embodiments, multiple stents, such as at least 2, 3, 4, 5, or more stents can be delivered during a single procedure using a multi-stent delivery system, such as, for example, described and illustrated in FIGS. 1-8G and paragraphs [0008] to [0059] of U.S. Pat. Pub. No. 2008/0234799 to Acosta et al. and FIGS. 1-10 and paragraphs [0015] to [0070] of U.S. Pat. Pub. No. 2008/0255653 to Schkolnik, both of which are hereby incorporated by reference in their entireties. In some embodiments, each stent can be placed approximately 3-10 mm, such as about 5 mm apart on the delivery catheter. In some embodiments, the delivery system includes a detachment mechanism, such as a cutting element such that a single stent can be cut into several shorter segments using the same delivery system. The delivery system can also include radiopaque marker elements between each stent to further facilitate delivery under fluoroscopy.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially and the individual components of the devices may be combined permanently or be designed for removable attachment at the clinical site. Additionally, the skilled artisan will recognize that any of the above-described methods can be carried out using any appropriate apparatus. Further, the disclosure herein of any particular feature in connection with an embodiment can be used in all other disclosed embodiments set forth herein. Thus, it is intended that the scope of the present invention herein disclosed should not be limited by the particular disclosed embodiments described above.

What is claimed is:

1. An intraluminal prosthesis, comprising:
a first end, a second end, and an elongate tubular body with a lumen therethrough;
a first layer comprising flexible interbraided filaments, wherein a first group of filaments comprise a biodegradable material and a second group of filaments comprise a metallic material;
a second layer of a porous thermoplastic material operably attached to the first layer; and
a third layer comprising a first bioactive agent,
wherein the prosthesis has a first cross-sectional outer diameter at the first end, a second cross-sectional outer diameter at the second end, and a third cross-sectional outer diameter at a mid-point on the prosthesis axially displaced from the first end and the second end of the prosthesis, wherein the prosthesis is configured such that the first end and the second end both comprise a first wall, wherein a portion of the first wall is folded over to form a second wall, wherein the second wall is secured to the first wall, wherein the first cross-sectional outer diameter and the second cross-sectional outer diameter are both larger than the third cross-sectional outer diameter when the prosthesis is in a first, radially compressed configuration for delivery as well as when the prosthesis is in a second, radially enlarged configuration within a blood vessel, wherein the prosthesis has a continuous, cylindrical cross-sectional inner diameter throughout its axial length, wherein the prosthesis comprises a bioactive agent reservoir between the first wall and the second wall, wherein the bioactive agent reservoir comprises a second bioactive agent.

2. The prosthesis of claim 1, comprising a total of 10-36 flexible interbraided filaments.

3. The prosthesis of claim 1, wherein the first group of filaments comprising a biodegradable material make up 70% or more of the total number of filaments and the second group of filaments make up 30% or less of the total number of filaments.

4. The prosthesis of claim 1, wherein the second layer is the outer layer relative to the first layer.

5. The prosthesis of claim 1, wherein the second layer is the inner layer relative to the first layer.

6. The prosthesis of claim 1, wherein the second group of filaments make up less than about 20% of the total number of filaments.

7. The prosthesis of claim 1, wherein the second group of filaments make up less than about 10% of the total number of filaments.

8. The prosthesis of claim 1, wherein the second group of filaments comprise strands that are interspersed at regular intervals with the strands of the first group of filaments.

9. The prosthesis of claim 1, wherein the second group of filaments comprise strands that are interspersed at irregular intervals with the strands of the first group of filaments.

10. The prosthesis of claim 1, wherein the first cross-sectional outer diameter is at least about 1% larger than the third cross-sectional outer diameter.

11. The prosthesis of claim 1, wherein the first cross-sectional outer diameter is at least about 3% larger than the third cross-sectional outer diameter.

12. The prosthesis of claim 1, wherein the first cross-sectional outer diameter is at least about 5% larger than the third cross-sectional outer diameter.

13. The prosthesis of claim 1, wherein the first cross-sectional outer diameter is at least about 7% larger than the third cross-sectional outer diameter.

14. The prosthesis of claim 1, wherein the first cross-sectional outer diameter is at least about 0.002 inches to 0.010 inches larger than the third cross-sectional outer diameter.

15. The prosthesis of claim 1, wherein the first group of filaments are wound in a first common direction but axially displaced relative to each other, wherein the second group of filaments are wound in a second common direction but axially displaced relative to each other, wherein the second common direction is opposite the first common direction.

16. The prosthesis of claim 1, wherein the second bioactive agent comprises a drug.

17. The prosthesis of claim 16, wherein the drug is selected from the group consisting of: paclitaxel, rapamycin, zotarolimus, and tacrolimus.

18. The prosthesis of claim 16, wherein the second bioactive agent comprises a stem cell.

* * * * *